United States Patent
McConnell

(10) Patent No.: US 11,013,612 B2
(45) Date of Patent: May 25, 2021

(54) FIXATION DEVICES FOR ANTERIOR LUMBAR OR CERVICAL INTERBODY FUSION

(71) Applicant: Institute for Musculoskeletal Science and Education, Ltd., Wayne, PA (US)

(72) Inventor: Jeffrey R. McConnell, Allentown, PA (US)

(73) Assignee: Institute for Musculoskeletal Science and Education, Ltd., King of Prussia, PA (US)

(*) Notice: Subject to any disclaimer, the term of this patent is extended or adjusted under 35 U.S.C. 154(b) by 0 days.

(21) Appl. No.: 15/996,189

(22) Filed: Jun. 1, 2018

(65) Prior Publication Data
US 2020/0093608 A1    Mar. 26, 2020

Related U.S. Application Data

(63) Continuation of application No. 14/017,099, filed on Sep. 3, 2013, now Pat. No. 9,987,142.
(Continued)

(51) Int. Cl.
*A61F 2/44* (2006.01)
*A61F 2/30* (2006.01)
(Continued)

(52) U.S. Cl.
CPC ............ *A61F 2/447* (2013.01); *A61F 2/4455* (2013.01); *A61B 17/8033* (2013.01);
(Continued)

(58) Field of Classification Search
CPC ........ A61F 2/446; A61F 2/4465; A61F 2/447; A61F 2/4455; A61F 2002/4475
See application file for complete search history.

(56) References Cited

U.S. PATENT DOCUMENTS

| | | |
|---|---|---|
| 5,609,635 A | 3/1997 | Michelson |
| 5,683,394 A | 11/1997 | Rinner |
| (Continued) | | |

FOREIGN PATENT DOCUMENTS

| | | |
|---|---|---|
| WO | 2010/092893 A1 | 8/2010 |
| WO | 2010092893 | 8/2010 |
| WO | 2016210434 | 12/2016 |

OTHER PUBLICATIONS

International Search Report and Written Opinion dated Jan. 12, 2018 for International Patent Application No. PCT/US2017/56973.
(Continued)

*Primary Examiner* — Julianna N Harvey
(74) *Attorney, Agent, or Firm* — Plumsea Law Group, LLC

(57) ABSTRACT

An implant including a cage configured to be implanted between two vertebrae, including a first deployable keel, including a first blade, a first flange extending substantially perpendicularly from a first edge of the first blade, and a second flange extending substantially perpendicularly from a second edge of the first blade, such that the cross-section of the first deployable keel is in the shape of half of an I-beam. The implant further includes a second deployable keel, including a second blade, a third flange extending substantially perpendicularly from a first edge of the second blade, and a fourth flange extending substantially perpendicularly from a second edge of the second blade, such that the cross-section of the second deployable keel is in the shape of half of an I-beam. The first keel is configured to deploy in a superior direction, and the second keel is configured to deploy in an inferior direction.

11 Claims, 16 Drawing Sheets

Related U.S. Application Data

(60) Provisional application No. 61/695,789, filed on Aug. 31, 2012.

(51) Int. Cl.
*A61B 17/80* (2006.01)
*A61F 2/28* (2006.01)

(52) U.S. Cl.
CPC ... *A61F 2/30749* (2013.01); *A61F 2002/2835* (2013.01); *A61F 2002/30166* (2013.01); *A61F 2002/30383* (2013.01); *A61F 2002/30387* (2013.01); *A61F 2002/30426* (2013.01); *A61F 2002/30485* (2013.01); *A61F 2002/30523* (2013.01); *A61F 2002/30579* (2013.01); *A61F 2002/30787* (2013.01); *A61F 2002/30884* (2013.01)

(56) References Cited

U.S. PATENT DOCUMENTS

| | | |
|---|---|---|
| 5,702,391 A | 12/1997 | Lin |
| 5,800,547 A | 9/1998 | Schafer et al. |
| 5,800,550 A | 9/1998 | Sertich |
| 6,102,950 A | 8/2000 | Vaccaro |
| 6,113,638 A | 9/2000 | Williams |
| 6,179,873 B1 | 1/2001 | Zientek |
| 6,251,140 B1 | 6/2001 | Marino |
| 6,447,546 B1 | 9/2002 | Bramlet |
| 6,478,823 B1 | 11/2002 | Michelson |
| 6,520,993 B2 | 2/2003 | James et al. |
| 6,527,803 B1 | 3/2003 | Crozet et al. |
| 6,726,720 B2 | 4/2004 | Ross et al. |
| 6,767,367 B1 | 7/2004 | Michelson |
| 6,800,092 B1 | 10/2004 | Williams |
| 7,214,243 B2 | 5/2007 | Taylor |
| 7,217,293 B2 | 5/2007 | Branch, Jr. |
| 7,223,289 B2 | 5/2007 | Trieu |
| 7,569,074 B2 | 8/2009 | Eisermann |
| 7,594,931 B2 | 9/2009 | Louis |
| 7,594,932 B2 | 9/2009 | Aferzon |
| 7,655,046 B2 | 2/2010 | Dryer |
| 7,749,274 B2 | 7/2010 | Razian |
| 7,771,475 B2 | 8/2010 | Michelson |
| 7,879,099 B2 | 2/2011 | Zipnick |
| 7,972,365 B2 | 7/2011 | Michelson |
| 7,981,157 B2 | 7/2011 | Castleman et al. |
| 7,998,211 B2 | 8/2011 | Baccelli et al. |
| 8,062,375 B2 | 11/2011 | Glerum |
| 8,070,812 B2 | 12/2011 | Keller |
| 8,070,819 B2 | 12/2011 | Aferzon |
| 8,075,618 B2 | 12/2011 | Trieu |
| 8,080,062 B2 | 12/2011 | Armstrong et al. |
| 8,100,972 B1 | 1/2012 | Bruffey |
| 8,142,508 B1 | 3/2012 | Bruffey |
| 8,147,556 B2 | 4/2012 | Louis |
| 8,182,539 B2 | 5/2012 | Tyber et al. |
| 8,216,313 B2 | 7/2012 | Moore |
| 8,221,502 B2 | 7/2012 | Branch, Jr. |
| 8,257,439 B2 | 9/2012 | Zeegers |
| 8,267,997 B2 | 9/2012 | Colleran |
| 8,273,125 B2 | 9/2012 | Baccelli et al. |
| 8,292,958 B1 | 10/2012 | Bruffey |
| 8,328,870 B2 | 12/2012 | Patel |
| 8,343,219 B2 | 1/2013 | Allain |
| 8,366,774 B1 | 2/2013 | Bruffey |
| 8,377,138 B2 | 2/2013 | Reo |
| 8,409,285 B2 | 4/2013 | Keller |
| 8,460,388 B2 | 6/2013 | Kirwan |
| 8,491,658 B1 | 7/2013 | Etminan |
| 8,512,409 B1 | 8/2013 | Mertens et al. |
| 8,518,120 B2 | 8/2013 | Glerum |
| 8,523,946 B1 | 9/2013 | Swann |
| 8,556,979 B2 | 10/2013 | Glerum |
| 8,679,183 B2 | 3/2014 | Glerum |
| 8,685,098 B2 | 4/2014 | Glerum |
| 8,698,405 B2 | 4/2014 | Kirwan |
| 8,709,086 B2 | 4/2014 | Glerum |
| 8,864,833 B2 | 10/2014 | Glerum |
| 8,888,853 B2 | 11/2014 | Glerum |
| 8,888,854 B2 | 11/2014 | Glerum |
| 8,968,405 B2 | 3/2015 | Kirwan et al. |
| 9,039,771 B2 | 5/2015 | Glerum |
| 9,198,774 B2 | 12/2015 | Pisharodi |
| 9,463,091 B2 | 10/2016 | Brett |
| 9,566,163 B2 | 2/2017 | Suddaby et al. |
| 9,675,470 B2 | 6/2017 | Packer et al. |
| 9,707,100 B2 | 7/2017 | Duffield et al. |
| 9,730,802 B1 | 8/2017 | Harvey |
| 2003/0109928 A1 | 6/2003 | Pasquet |
| 2003/0187436 A1 | 10/2003 | Bolger et al. |
| 2004/0254644 A1 | 12/2004 | Taylor |
| 2005/0027362 A1 | 2/2005 | Williams et al. |
| 2005/0033429 A1 | 2/2005 | Kuo |
| 2005/0049590 A1 | 3/2005 | Alleyne |
| 2005/0107788 A1 | 5/2005 | Beaurain |
| 2005/0125062 A1 | 6/2005 | Biedermann et al. |
| 2005/0197760 A1 | 9/2005 | Kaga |
| 2006/0069436 A1 | 3/2006 | Sutton et al. |
| 2006/0282074 A1 | 12/2006 | Renaud |
| 2007/0162130 A1 | 7/2007 | Rashbaum |
| 2007/0270961 A1 | 11/2007 | Ferguson |
| 2008/0021562 A1 | 1/2008 | Huppert |
| 2008/0051901 A1 | 2/2008 | deVilliers |
| 2008/0051902 A1 | 2/2008 | Dwyer |
| 2008/0133017 A1 | 6/2008 | Beyar et al. |
| 2008/0234686 A1 | 9/2008 | Beaurain |
| 2008/0312743 A1 | 12/2008 | Vila |
| 2009/0164020 A1 | 6/2009 | Janowski |
| 2009/0182430 A1 | 7/2009 | Tyber |
| 2009/0265007 A1 | 10/2009 | Colleran |
| 2009/0292316 A1 | 11/2009 | Hess |
| 2010/0010547 A1 | 1/2010 | Beaurain |
| 2010/0016974 A1 | 1/2010 | Janowski |
| 2010/0145459 A1 | 6/2010 | McDonough et al. |
| 2010/0185289 A1* | 7/2010 | Kirwan ............... A61F 2/4455 623/17.11 |
| 2010/0185292 A1* | 7/2010 | Hochschuler ......... A61F 2/4455 623/17.16 |
| 2010/0204737 A1* | 8/2010 | Bae ...................... A61F 2/4455 606/279 |
| 2010/0249935 A1 | 9/2010 | Slivka |
| 2010/0280618 A1 | 11/2010 | Jodaitis |
| 2010/0305704 A1 | 12/2010 | Messerli |
| 2011/0015742 A1 | 1/2011 | Hong |
| 2011/0015745 A1 | 1/2011 | Bucci |
| 2011/0035007 A1* | 2/2011 | Patel .................... A61F 2/4611 623/17.11 |
| 2011/0077739 A1 | 3/2011 | Rashbaum |
| 2011/0093074 A1 | 4/2011 | Glerum et al. |
| 2011/0098747 A1* | 4/2011 | Donner ............. A61B 17/8042 606/264 |
| 2011/0118840 A1 | 5/2011 | Huntsman |
| 2011/0160866 A1* | 6/2011 | Laurence .............. A61F 2/4455 623/17.16 |
| 2011/0166655 A1 | 7/2011 | Michelson |
| 2011/0208311 A1 | 8/2011 | Janowski |
| 2011/0230970 A1 | 9/2011 | Lynn et al. |
| 2011/0230971 A1 | 9/2011 | Donner et al. |
| 2011/0313528 A1 | 12/2011 | Laubert |
| 2012/0035729 A1 | 2/2012 | Glerum |
| 2012/0053693 A1 | 3/2012 | Zeegers |
| 2012/0078371 A1 | 3/2012 | Gamache |
| 2012/0078373 A1* | 3/2012 | Gamache ............. A61F 2/4455 623/17.16 |
| 2012/0095559 A1 | 4/2012 | Woods et al. |
| 2012/0116466 A1 | 5/2012 | Dinville |
| 2012/0116486 A1 | 5/2012 | Naga et al. |
| 2012/0150300 A1 | 6/2012 | Nihalani |
| 2012/0150304 A1 | 6/2012 | Glerum |
| 2012/0150305 A1 | 6/2012 | Glerum |
| 2012/0158146 A1 | 6/2012 | Glerum |
| 2012/0158148 A1 | 6/2012 | Glerum |
| 2012/0185049 A1 | 7/2012 | Varela |

(56) References Cited

U.S. PATENT DOCUMENTS

| | | | |
|---|---|---|---|
| 2012/0191196 A1 | 7/2012 | Louis | |
| 2012/0215315 A1* | 8/2012 | Hochschuler | A61F 2/4455 623/17.16 |
| 2012/0265248 A1 | 10/2012 | Delecrin | |
| 2012/0277867 A1* | 11/2012 | Kana | A61F 2/4465 623/17.16 |
| 2012/0330417 A1 | 12/2012 | Zipnick | |
| 2012/0330424 A1 | 12/2012 | Zeegers | |
| 2013/0013006 A1 | 1/2013 | Rashbaum | |
| 2013/0041408 A1 | 2/2013 | Dinville | |
| 2013/0053891 A1 | 2/2013 | Hawkins | |
| 2013/0110242 A1 | 5/2013 | Kirwan | |
| 2013/0150968 A1 | 6/2013 | Dinville | |
| 2013/0166029 A1* | 6/2013 | Dinville | A61F 2/44 623/17.16 |
| 2013/0268076 A1 | 10/2013 | Carlson et al. | |
| 2013/0310935 A1 | 11/2013 | Swann | |
| 2013/0338776 A1 | 12/2013 | Jones | |
| 2014/0074214 A1 | 3/2014 | Raje et al. | |
| 2014/0074241 A1 | 3/2014 | McConnell | |
| 2014/0088711 A1* | 3/2014 | Chin | A61F 2/447 623/17.16 |
| 2014/0114420 A1 | 4/2014 | Robinson | |
| 2014/0148904 A1 | 5/2014 | Robinson | |
| 2014/0180417 A1 | 6/2014 | Bergey | |
| 2014/0236297 A1 | 8/2014 | Iott | |
| 2014/0303731 A1 | 10/2014 | Glerum | |
| 2014/0324171 A1 | 10/2014 | Glerum | |
| 2014/0379085 A1 | 12/2014 | Duffield et al. | |
| 2015/0012097 A1 | 1/2015 | Ibarra | |
| 2015/0127107 A1 | 5/2015 | Kim | |
| 2015/0202051 A1 | 7/2015 | Tanaka et al. | |
| 2015/0209089 A1 | 7/2015 | Chataigner et al. | |
| 2015/0250603 A9 | 9/2015 | Glerum | |
| 2015/0272743 A1 | 10/2015 | Jimenez et al. | |
| 2015/0305880 A1 | 10/2015 | Kim et al. | |
| 2015/0342754 A1 | 12/2015 | Geebelen et al. | |
| 2016/0038845 A1 | 2/2016 | Mizunaga et al. | |
| 2016/0058565 A1 | 3/2016 | Zappacosta et al. | |
| 2016/0338845 A1 | 11/2016 | Ashleigh | |
| 2016/0374831 A1 | 12/2016 | Duffield et al. | |
| 2017/0100260 A1 | 4/2017 | Duffield et al. | |
| 2017/0165082 A1 | 6/2017 | Faulhaber | |
| 2017/0165083 A1 | 6/2017 | Greenhalgh | |
| 2017/0266016 A1 | 9/2017 | Faulhaber | |
| 2017/0281358 A1 | 10/2017 | Wagner et al. | |
| 2017/0296238 A1 | 10/2017 | Snell et al. | |
| 2017/0303975 A1 | 10/2017 | Koch et al. | |
| 2018/0104068 A1 | 4/2018 | Sack | |
| 2018/0110627 A1 | 4/2018 | Sack | |

OTHER PUBLICATIONS

International Search Report and Written Opinion dated Jan. 23, 2018 for International Patent Application No. PCT/US2017/058109.

International Search Report and Written Opinion dated Dec. 18, 2019 for International Patent Application No. PCT/US2019/47714.

Office Action dated Apr. 9, 2020, in U.S. Appl. No. 16/109,326.

Supplementary Partial European Search Report for EP 17 86 5409, dated Jun. 19, 2020 (17 pp).

Supplementary Partial European Search Report for EP 17 86 3072, dated Jun. 25, 2020 (17 pp).

Extended European Search Report dated Oct. 30, 2020 in EP 17865409.

Office Action dated Nov. 30, 2020 in CN 2017800805892.

* cited by examiner

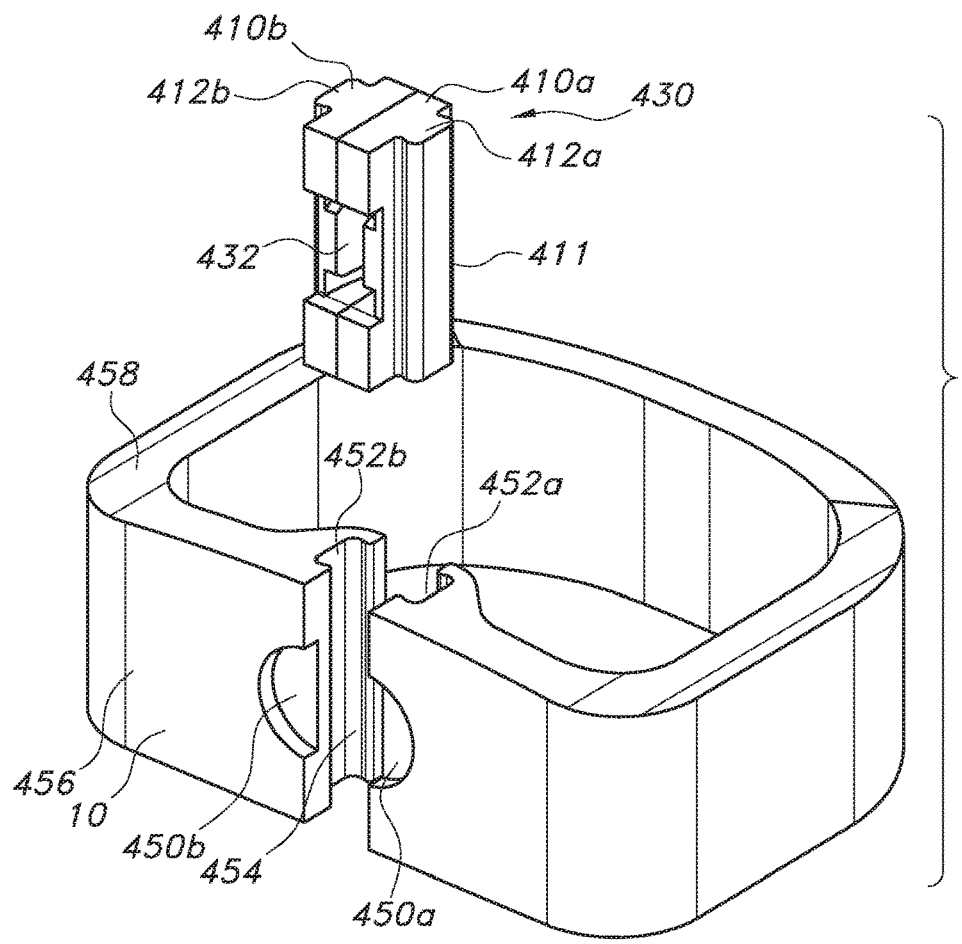
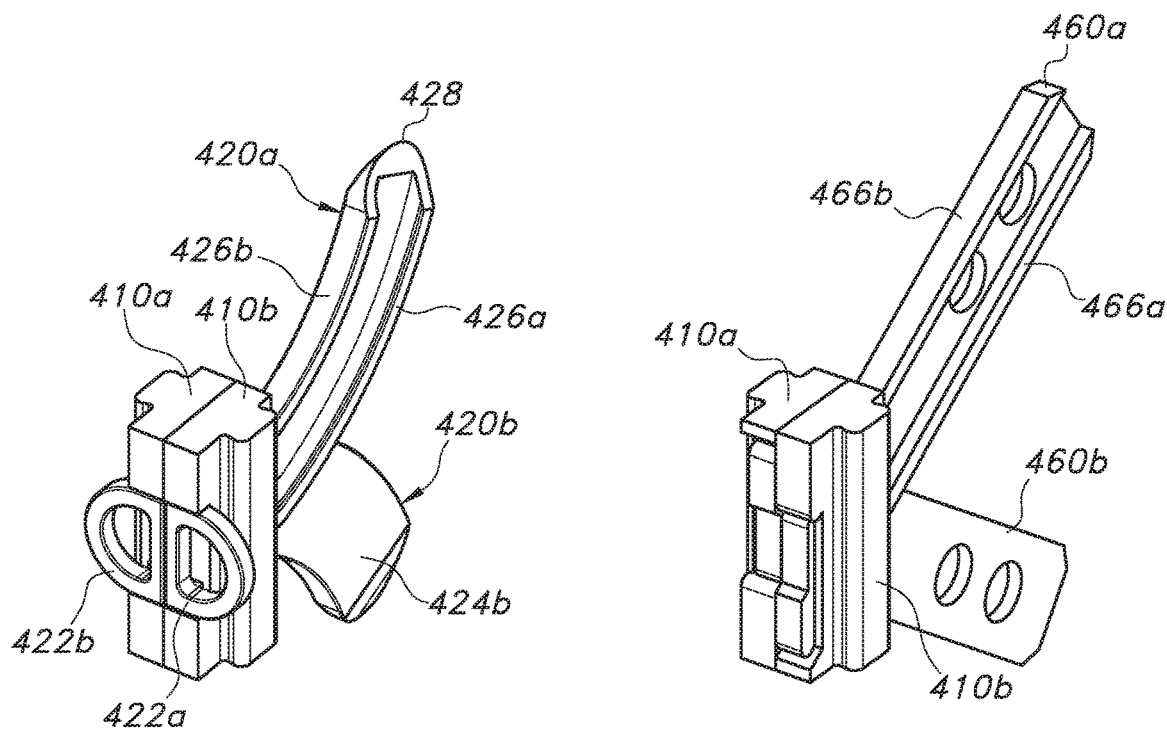
FIG. 4A
FIG. 4B
FIG. 4C

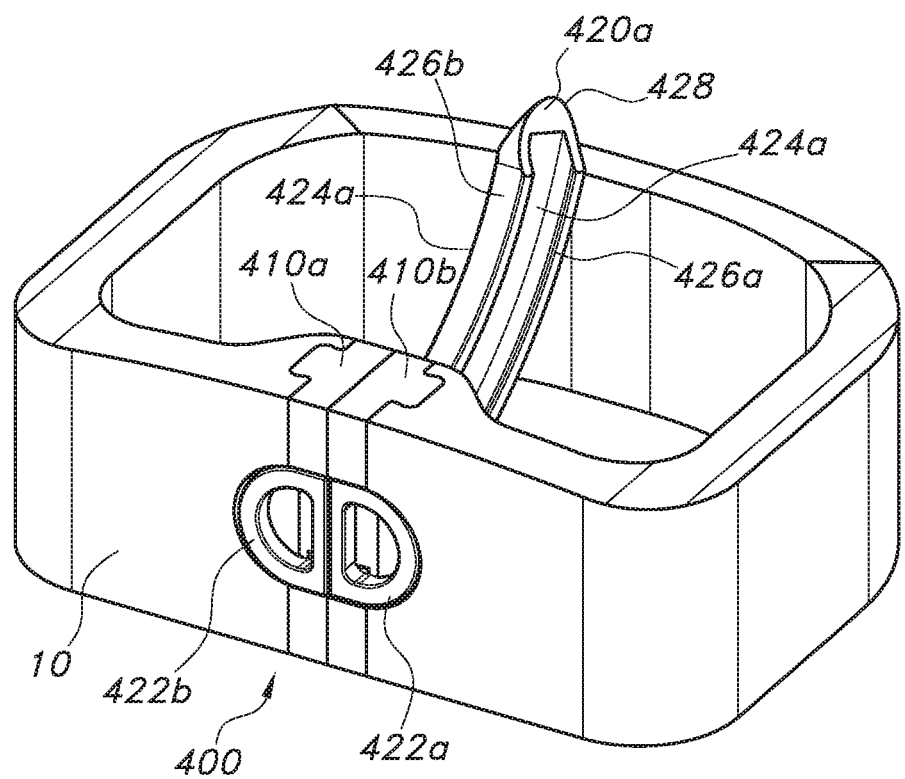
FIG. 4D
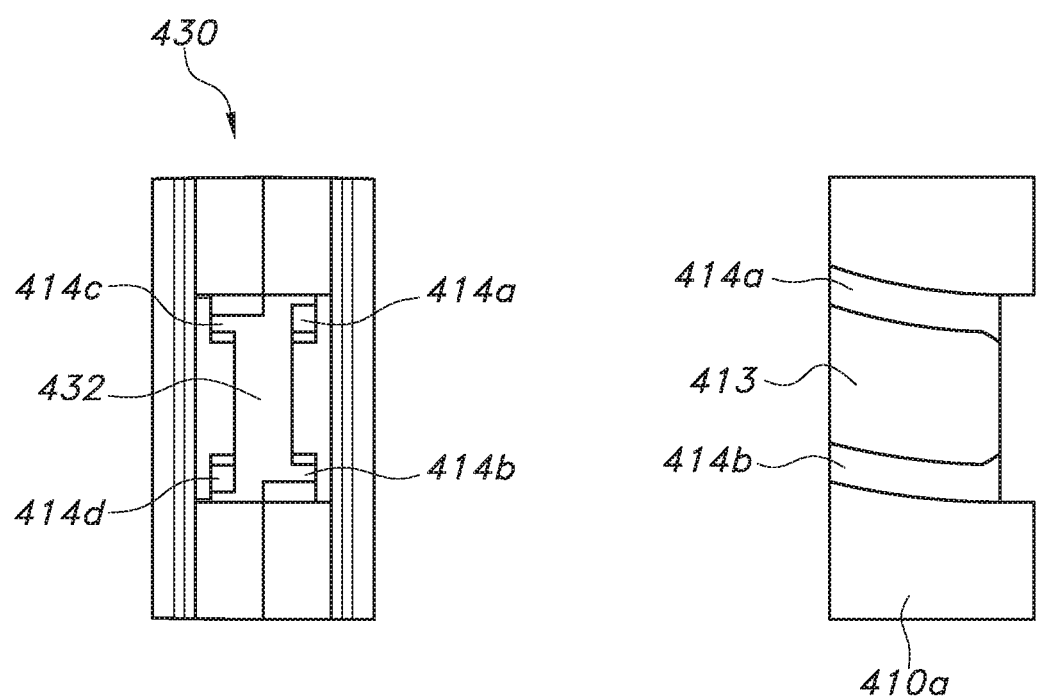
FIG. 4E
FIG. 4F

FIXATION DEVICES FOR ANTERIOR LUMBAR OR CERVICAL INTERBODY FUSION

CROSS-REFERENCE TO RELATED APPLICATION

This application is a continuation of McConnell, U.S. Patent Application Publ. No. 2014/0074241, published on Mar. 13, 2014, and which claims priority to U.S. Provisional application Ser. No. 61/695,789, filed Aug. 31, 2012. The entire disclosures of these applications are incorporated herein by reference.

FIELD OF THE INVENTION

This invention relates to devices and methods used in spine surgery, particularly devices and methods used to stabilize cages used in interbody fusions, such as anterior lumbar interbody fusions (ALIF) and lateral interbody fusions (LIF).

BACKGROUND OF THE INVENTION

Anterior lumbar interbody fusion (ALIF) is a type of spinal fusion that utilizes an anterior (front—through the abdominal region) approach to fuse the lumbar spine bones together. The intervertebral disc is removed and replaced with a bone (or metal) spacer, in this case using an anterior approach. The anterior technique is often favored when multiple spinal levels are being fused and multiple discs need to be removed. ALIF may be performed in conjunction with or without a posterior decompression (laminectomy) and/or instrumentation (use of metal screws/rods). The anterior approach is also ideal when only one spinal level is fused and a posterior decompression and/or instrumentation are not required. Although the anterior lumbar approach involves retracting (moving out of the way, temporarily) large blood vessels (aorta, vena cava) and the intestines, there is a wide exposure of the intervertebral disc without retraction of the spinal nerves and neurologic structures (and therefore, a decreased risk of neurologic injury).

ALIF is commonly performed for a variety of painful spinal conditions, such as spondylolisthesis and degenerative disc disease, among others.

The ALIF approach is advantageous in that, unlike the PLIF and posterolateral gutter approaches, both the back muscles and nerves remain undisturbed.

Another advantage is that placing the bone graft in the front of the spine places it in compression, and bone in compression tends to fuse better.

Lastly, a much larger implant can be inserted through an anterior approach, and this provides for better initial stability of the fusion construct.

However, the ALIF procedure also involves resection of the anterior longitudinal ligament, which can destabilize the implanted cage.

Therefore, surgeons often combine ALIF with a posterior approach (anterior/posterior fusions) because of the need to provide more rigid fixation than an anterior approach alone currently provides. Additionally, stabilization and fixation devices have been added to a standard interbody fusion spacer to stabilize and fix the spacer in place.

The lateral approach (LIF) provides an alternate route to the spine that disturbs fewer structures and tissues. This, in combination with small incisions, means much less discomfort for the patient and fewer risks of complications. With a lateral interbody fusion, the surgeon approaches the back through a small incision in the side of the body, using special tools and techniques. There are a number of other names for the same technique, including DLIF® (Direct Lateral Interbody Fusion), XLIF® (eXtreme Lateral Interbody Fusion), and transpsoas interbody fusion.

In most cases, patients who are candidates for this surgery are those who would have needed an incision in the abdomen in order for the surgeon to reach the area of concern. Approaching the spine through the abdomen means the surgeon must get around large blood vessels, nerves, muscles, and organs that are in the way. This can prolong recovery following surgery and, in rare cases, can cause complications such as nerve or blood vessel damage.

Many existing interbody fusion spacer systems require multiple actions on the part of the surgeon with respect to cage insertion, and fixation of the cage to the vertebral bodies.

For example, the INDEPENDENCE® Spacer System (Globus Medical, Inc.) integrates a stabilization plate and a PEEK interbody spacer into a preassembled system. INDEPENDENCE® also incorporates a smooth screw blocking mechanism, minimizing disruption to the anatomy surrounding the surgical site and may lessen the long term impact from surgery. However, this system requires multiple actions by a surgeon to insert and fix it in place.

Additionally the use of a screw fixation system has a number of disadvantages. Screw fixation systems can require the use of a drill or an awl to prepare a hole in the vertebrae. Some screw systems require two different length screwdrivers to insert the screw or an initial driver to insert the screw most of the way into the vertebrae and then a torque driver to do the final tightening.

Screw fixation devices require a specific angle of insertion that requires a larger soft tissue exposure/corridor than necessary to insert the cage itself. Sometimes these angles require undue pressure on the surrounding soft tissues which could place abdominal viscera and blood vessels at risk. These fixed angles required to insert the screws can limit the ability to insert the fixation devices at the L5-S1 disc where the symphysis pubis may inhibit access.

Additionally, the fixed angles for screw insertion and limited soft tissue exposure can place excess pressure on the insertion tool and cause the screw to be inserted inappropriately and possibly strip the screw at the bone-screw interface or the screw-anterior plate interface. This may occur if the device screw uses a separate machine thread to lock the screw to the cage.

While overcoming some of the limitations associated with fixed-angle screw insertion some vertebral fixation systems utilize variable angle screw insertion, however these systems may not provide rigid fixation to the plate/cage and vertebrae. This may allow micro motion and increase the risk of failed fusion.

Screw systems, fixed or variable angle, provide little surface area contact within the vertebra to adequately resist the forces of flexion, extension, rotation, and translation/shear. A fixation system that effectively neutralizes these forces is necessary for rigid fixation. Rigid fixation eliminates the need for supplemental external immobilization devices (braces) and allows early patient mobilization and return to more normal activity.

Instrumentation and specialized tools for insertion of an intervertebral implant is yet another design parameter to consider when designing a spacer. Spinal fusion procedures can present several challenges because of the small clearances around the spacer when it is being inserted into position. For instance, the instrumentation used may securely grip the implant on opposing sides or surfaces. In U.S. Pat. No. 6,520,993 to James, et al., for example, the superior and inferior surfaces have one or more regions in which no gripping teeth are present. These protrusion-free zones enable the implant to be grasped and manipulated by elongate rectangular blades. However, the clearance required to insert the spacer must be higher than the spacer itself to accommodate the required instrumentation. For this reason, distraction of the treated area typically is greater than the implant itself.

Similarly, when the gripping tools used to manipulate and insert the implant on the sides of the spacer, additional clearance typically is needed to accommodate the added width of the insertion tool blades. Such increases in height or width of the profile of the spacer, when in communication with instrumentation, means that additional space is needed in order to insert the spacer. In some circumstances, providing for this additional clearance space can be difficult to achieve.

Thus, despite known devices that promote fusion of a treated area of the spine, there remains a need for improved fixation devices for use in interbody fusions, such as ALIF and anterior cervical discectomy and fusion.

Therefore it is an object of the invention to provide improved fixation devices and kits for interbody cages.

It is a further object of the invention to provide improved methods for achieving vertebral interbody fusions, in the lumbar or cervical spine.

SUMMARY OF THE INVENTION

Fixation systems, kits and methods for vertebral interbody fusions are provided herein. The fixation systems fix an intervertebral cage in its desired location, typically in the lumbar or cervical spine, such that the cage resists left to right rotation and resists flexion and/or extension. Additionally, the fixation elements are locked in place to prevent accidental removal from the cage. In one embodiment, the fixation system contains two deployable blades (also referred to herein as keels) that are insertable into an attachment portion or an anterior wall of an intervertebral cage. Each keel contains a blade with two flanges, wherein the cross-section of the keels is in the shape of half of an I-beam. In some embodiments the anterior wall is permanently attached to the cage. In others it is an attachment portion that is configured to be received by and attached to an intervertebral cage. The attachment portion may be one piece or two or more pieces that mate to form the attachment portion. In one embodiment, the attachment portion is formed from two pieces that form an I-beam with a central opening, where the central opening is configured to receive both of the blades.

The blades can straight or curved. Following insertion into the cage, the blades insert into the superior and inferior vertebral bodies.

In a second embodiment, two blades are insertable into the superior and inferior sides of a cage, such as by sliding the blades in a channel that mates with the bottom, attachment portion on the blades. The blades can be integral or separate from a front plate, which locks onto the anterior portion of the cage. In a preferred embodiment, the blades are integral with the front plate and the system contains an inner plate with one or more holes for additional fixation elements, such as screws of fluted nails. Any of the systems may be modified to include further fixation elements, such as fluted nails, and/or additional locking elements.

BRIEF DESCRIPTION OF THE DRAWINGS

FIG. 2A is an anterior perspective view of a keel. FIG. 2B is a coronal cross-sectional view of the cage with deployable keels, particularly illustrating the screw shaft and gear mechanism. FIG. 2C is a front view of the ALIF cage containing deployable blades. FIG. 2D is partial internal left side view of the device. FIG. 2E is a top view of a horizontal cross-section of the device.

FIG. 3A is an anterior perspective view of the ALIF cage with an inner plate attached to the anterior portion of the cage. FIG. 3B is the same perspective view as shown in FIG. 3A, with two fixation elements, such as superior and inferior fluted nails, inserted therein. FIG. 3C is a perspective view of the fixation device, including the two fixation elements, also showing the insertion of the outer plate with two keels into the cage. FIG. 3D is a perspective view of the fully assembled fixation device.

FIGS. 4A-4F are different views of an ALIF cage with I-beam fixation and two keels. FIG. 4A is an exploded view of the I-beam attachment portion and the ALIF cage. FIG. 4B is a perspective view of the I-beam attachment portion with the keels attached, where the blades of the keels are curved. FIG. 4C is a perspective view of the I-beam attachment portion with the keels attached, where the blades of the keels are straight. FIG. 4D is an anterior perspective view of the fixation device. FIG. 4E is a front plan view of the I-beam attachment portion. FIG. 4F is a side view of the I-beam attachment portion showing the grooves.

FIG. 5A is a posterior view of the locking element. FIG. 5B is a posterior perspective view of the ALIF cage containing a front plate inserted therein. FIG. 5C is an anterior exploded view of the ALIF cage with two fixation elements and the locking element. FIG. 5D is a perspective view of the fully assembled fixation device.

FIG. 6A is an illustration of a locking element for three fixation elements, such as screws or fluted nails, in a cage. FIG. 6B is an illustration of a locking element for two fixation elements in a cage. FIG. 6C is an illustration of a further embodiment for a locking element for two fixation elements in a cage.

FIG. 7A is an illustration of a keel containing a locking tab. FIGS. 7B-7I are different views illustrating a keel locked inside a cavity of half of an I-beam attachment portion. FIG. 7B is a perspective view, FIG. 7C is a top view, FIG. 7D is a side view, and FIG. 7E is the opposite side view. FIG. 7F is a side view of the keel in a locked position in the half I-beam portion. FIG. 7G is the cross-sectional view taken at section line 7G-7G of FIG. 7F. FIG. 7H is a side view of the keel in an unlocked position in the half I-beam portion. FIG. 7I is the cross-sectional view taken at section line 7I-7I of FIG. 7H.

FIG. 8A is a top view of the cage. FIG. 8B is a side view of the cage. FIG. 8C is a side view of the cage with the blade tips proud.

FIGS. 9A and 9B illustrate the ALIF cage with the blades protruding out the anterior wall. FIGS. 9C and 9D illustrate the ALIF cage with the blades deployed so that they would be inserted into the superior vertebral body and the inferior vertebral body. FIG. 9A shows the lateral wall with the posterior side of the device at the top and the anterior side of the device at the bottom. FIG. 9B is a top view illustrating the deployable keels protruding from the anterior wall. FIG. 9C is a perspective view; FIG. 9D is a front view of the cage with the blades in a deployed position.

FIG. 10A is a side view of the cage with angled deployable keels. FIG. 10B is a coronal cross-sectional view of the cage with angled deployable keels taken at section line 10B-10B in FIG. 10A. FIG. 10C is a front view of the cage containing angled deployable keels.

DETAILED DESCRIPTION OF THE INVENTION

I. Fixation Systems

Figure 1A:
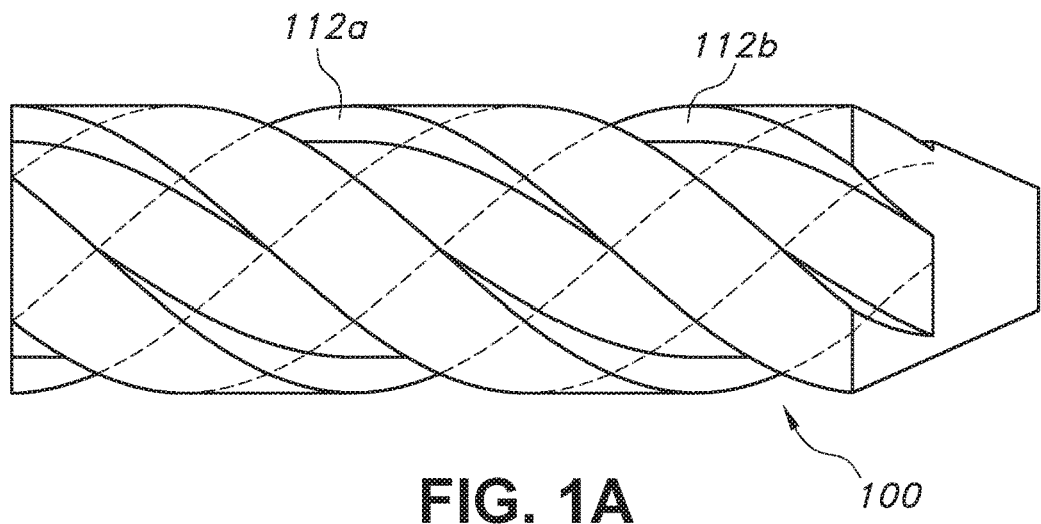
FIGS. 1A and 1B illustrate an exemplary fluted nail.

The fixation systems described herein fix an intervertebral cage in its desired location, to resist left to right rotation and to resist flexion and/or extension of the cage. Additionally, the fixation elements are locked in place to prevent accidental removal from the cage. When assembled, the implant is contained within the excised disc space and does not protrude past the anterior wall of the vertebral body. Thus the system has a zero anterior profile. Additionally, preparations of anterior surface of the vertebral body are minimized because the implant does not lie against this surface.

In some embodiments, the fixation system is preassembled. When the front plate and cage are preassembled, the plate is automatically aligned upon implant insertion. This simplifies the insertion process, preventing the need to align and realign the front plate.

The systems can be used for anterior, posterior or lateral approaches. The devices can be single-use or re-usable. In one embodiment only the keels are re-usable. In another embodiment, only the cage is reusable. The device may be removed from the patient, the keels discarded, and a new set of keels inserted into the device before the device is then re-inserted into the patient. In other instances, the entire device can be removed from the patient and then later re-inserted.

A. Cage

An intervertebral cage, having a three dimensional body suitable for insertion between vertebrae is provided. The cage serves as a spacer, to ensure that the desired distance between the vertebrae is maintained. The cage contains one or more openings, typically two openings for the insertion of bone graft material. The cages allow the bone graft to grow from the vertebral body through the cage and into the next vertebral body.

In addition to the features shown in the Figures, the cages and fixation systems may contain one or more threaded holes, slots or channels to mate with instruments to facilitate holding and inserting the implants.

The cage contains one or more areas for attaching or inserting one or more fixation elements to resist left to right rotation and to resist flexion and/or extension of the cage. Following insertion of the one or more fixation elements, the fixation elements remain in the resulting system, i.e. pull out and/or translation of the fixation elements is prevented.

The cage can be formed from any suitable biocompatible, non-degradable material with sufficient strength. Typical materials include titanium and inert, biocompatible polymers, such as polyether ether ketone (PEEK) (e.g. PEEK-OPTIMA®, Invibio Inc). Optionally, the cage contains a radiopaque marker to facilitate visualization during imaging.

In some embodiments, the wall or a portion thereof, through which the fixation elements are inserted or attached, is formed from a different material than the rest of the cage. For example, most of the cage depicted in FIGS. 9A-9D is generally formed from a first material, such as PEEK, while the anterior wall 912 of the cage is formed from a second, different material, such as titanium or another biocompatible material with a similar strength. Preferably, the anterior wall is affixed to the rest of the cage in a permanent manner.

Generally, the cage is adapted for insertion within an intervertebral space between a superior vertebral body and an inferior vertebral body and includes a first insertion end portion, a second end portion opposite the first end portion, a first lateral side portion, a second lateral side portion, an upper surface and a lower surface.

The upper and lower surfaces of the cage, which contact the superior vertebral body and the inferior vertebral body, typically contain teeth, knurling, ridges or similar projections, to aid in securing the implant to the vertebral endplate and preventing or reducing any shifting of the implant. This also provides initial stability following implantation.

The particular surface shape and curvature, or taper in the anterior-posterior direction as well as between the lateral side surfaces depends upon the location at which the cage is intended to be inserted. For example, the anterior:posterior dimension of the LIF cage is less than the anterior:posterior dimension of the ALIF cage to allow insertion from a lateral approach. Typical anterior:posterior dimensions for LIF cage range from about 18 to 24 mm, while for the ALIF, typical anterior:posterior dimensions range from about 26 to 31 mm. The left to right dimension of the LIF cage is typically longer than the left to right dimension in an ALIF cage so that it can span the entire width of the vertebral body. The shape of the perimeter of the cage can be modified for lumbar applications, or for other areas such as in the cervical area of the spine.

The cage and its fixation elements can be implanted in the desired location in a patient using known surgical instruments. The number and position of access through-holes, e.g. two, three, four or the like, is dictated by the particular patient's anatomy or other surgical considerations, and is also not intended to be limited by the type of attachment mechanism between the implant and instrumentation.

The implants described herein may be sized and configured for anterior, posterior or lateral approaches and insertion.

B. Fixation Elements

One or more fixation elements are provided for insertion into and/or attachment to the intervertebral cage. The fixation elements provide stabilization in flexion and lateral bending, and also in extension and rotation. The fixation elements are attached to the intervertebral cage to prevent them from slipping out or being pulled out of place, absent surgery or another method of intentional removal of the fixation elements.

Following insertion into a patient, and optionally deployment, the fixation elements anchor the cage into cancellous bone of at least one vertebral body.

1. Fluted Nail

Figure 1B:
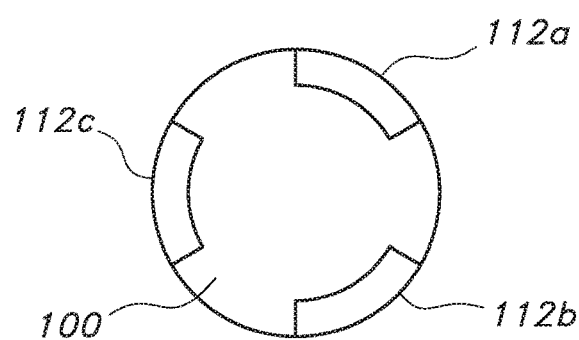

In one embodiment, the one or more fixation elements include one or more fluted nails, preferably at least two fluted nails. An exemplary fluted nail is illustrated in FIGS. 1A and 1B. As shown in FIGS. 1A and 1B, the fluted nail 100 contains one or more grooves (112a, b, c) that run along the length of the body of the nail in a helical pattern. As shown in FIG. 1B, the nail may contain three grooves. Typically the fluted nail contains at least two helical grooves, preferably the nail contains three helical grooves, optionally the nail contains more than three helical grooves. The fluted nail has longer pitch than standard threads on screws. Suitable pitches include 5-10 mm.

Fluted nails with suitable dimensions for placement in the cages and insertion into the proximal vertebra of the spine may be used. For example, the nail shank may range from about 4.5-6 mm in diameter and from about 20-40 mm in length. The head of the nail may range from about 5.5-7 mm in diameter, depending on the nail shank diameter. The depths from the grooves may range from about 1-1.5 mm.

In one embodiment the fixation elements include two fluted nails. In an alternative embodiment, the fixation elements include three fluted nails. In yet further alternative embodiments the fixation elements include at least one fluted nail, optionally two or more fluted nails, optionally three or more fluted nails, or optionally four or more fluted nails.

Figure 1C:
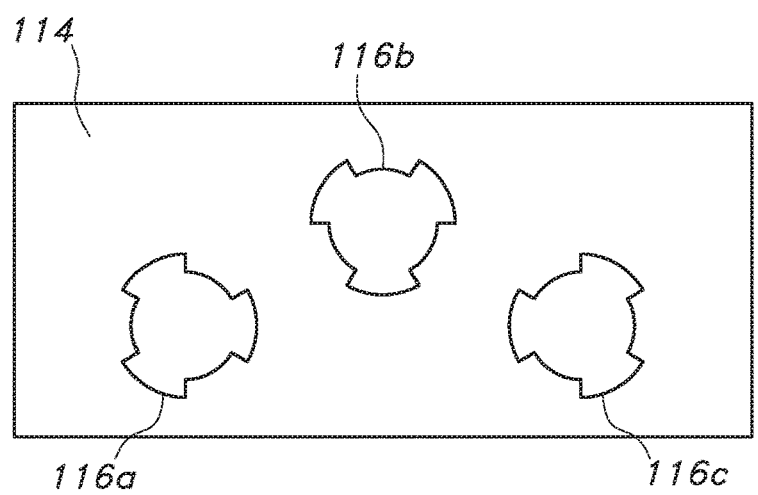
FIG. 1C illustrates a portion of a front plate with holes that mate and guide the fluted nails.

In some embodiments, the fixation system also includes a front plate 114 which affixes to the anterior side of the intervertebral cage (see FIG. 1C). In this embodiment, the front plate contains one or more, preferably two, openings (116a, b, c) with a shape that matches the cross-section of the body of the fluted nail (see, e.g. FIGS. 1B and 1C). The front plate can serve as a locking mechanism for the fluted nails by preventing the nails from unscrewing or sliding out of the hole into which it is inserted.

a. Insertion and Implantation

The fluted nail can be forced into place, such as using a hammer. As it is hammered in place, the fluted nail rotates along the path of grooves, as guided by the openings in the front plate, until the head of the nail is essentially flush with the outer surface of the front plate 114. This prevents the nail from backing out after it is inserted into the desired location. Additionally, the rotation of the nail during its placement compresses the surrounding bone, further restricting movement of the nail following placement.

2. Keel

In some embodiments, the one or more fixation elements include one or more bone engaging projections. Suitable bone engaging projections include but are not limited to blades, fins, spikes, keels, ridges, knurlings, or a combination thereof. Preferably the bone engaging projections are one or more keels, more preferably two keels. Following insertion, and, if necessary deployment, the distal tip of each keel extends above or below the cage and is inserted into the superior vertebral body or the inferior vertebral body to increase the stability of the cage. The keels can extend in a substantially perpendicular direction relative to the cage (i.e. approximately 90° relative to the upper and lower surfaces of the cage) or at a different angle relative to the upper and lower surfaces of the cage. The keels that are deployed at an angle other than 90° can be longer than the keels that extend in a direction that is generally perpendicular to the upper and lower surfaces of the cage. The longer keels increase the stability of the cage relative to the same cage with keels deployed at a substantially 90° angle.

Typically when deployed, each keel protrudes about 3 to 6 mm past the superior and inferior surfaces of the cage.

The keels can have any suitable geometry that allows them to insert into the proximal vertebral body and remain in place. In one embodiment the keels are substantially straight (460a, 460b); in another embodiment the keels are curved (420a, 420b). In one embodiment, keels with different geometries are provided in a kit. This allows a user to select the appropriate keel for the patient. For example, a surgeon may select to use one curved keel and one straight keel, or two curved keels or two straight keels. The radius of curvature can vary. The radius of curvature is preferably selected to provide a sufficient length of keel that penetrates the bone, while also maintaining the blade within confines of the cage.

Preferably each keel contains a blade with two flanges, wherein the cross-section of the keels is in the shape of half of an I-beam.

a. Deployable Keel(s)

i. Deployed by Pushing

In one embodiment, the keels are inserted into the cage in slidable relation to the cage, such that in the initial position, the keels protrude out of the anterior wall. When the keels are deployed, they are pushed through the anterior wall, such that the tips of the keels pass through the inside of the cage, exit the cage, and extend into the proximal superior or inferior vertebral body. The height and shape of the cage and keels is selected such that following implantation and deployment of the keels, the cage and the keels do not add to the anterior profile of the vertebral column.

(1.) Keels

Figure 9A:
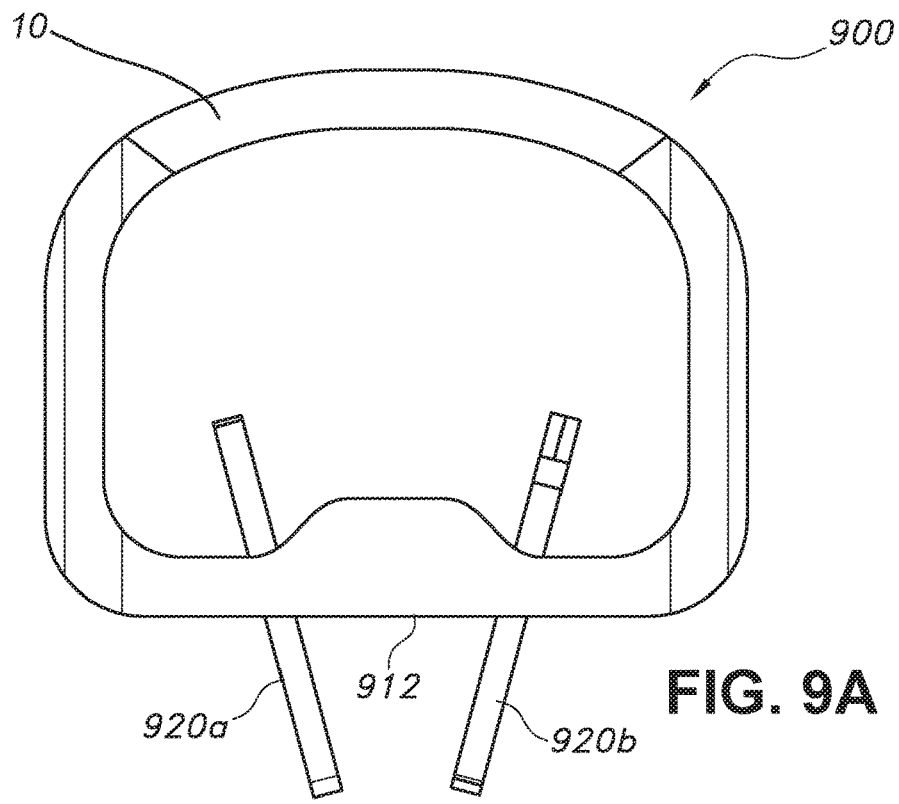
FIGS. 9A-9D are different views of an ALIF cage with deployable blades (also referred to as keels).
Figure 9B:
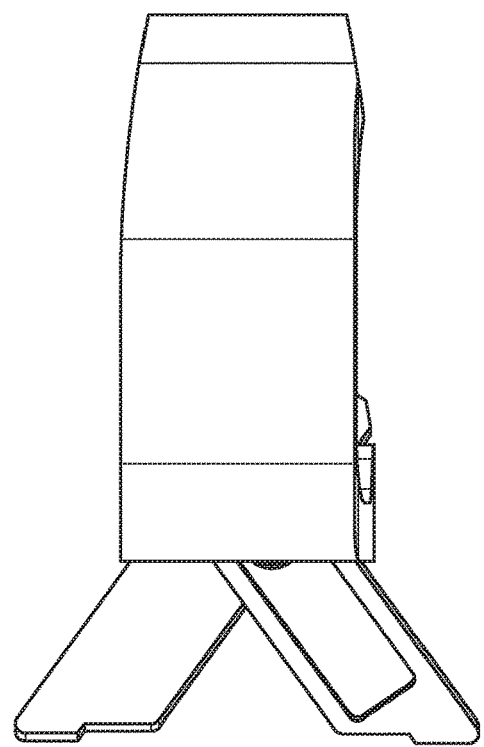

As shown in FIGS. 9A and 9B, relatively long keels, such as keels ranging in length from about 5 mm to about 10 mm, can be used in devices into which the keels are insertable into and through the anterior wall 912. In this embodiment, when initially inserted, the keels (920a and 920b) protrude out the anterior wall 912. See, e.g., FIGS. 9A and 9B.

Figure 9C:
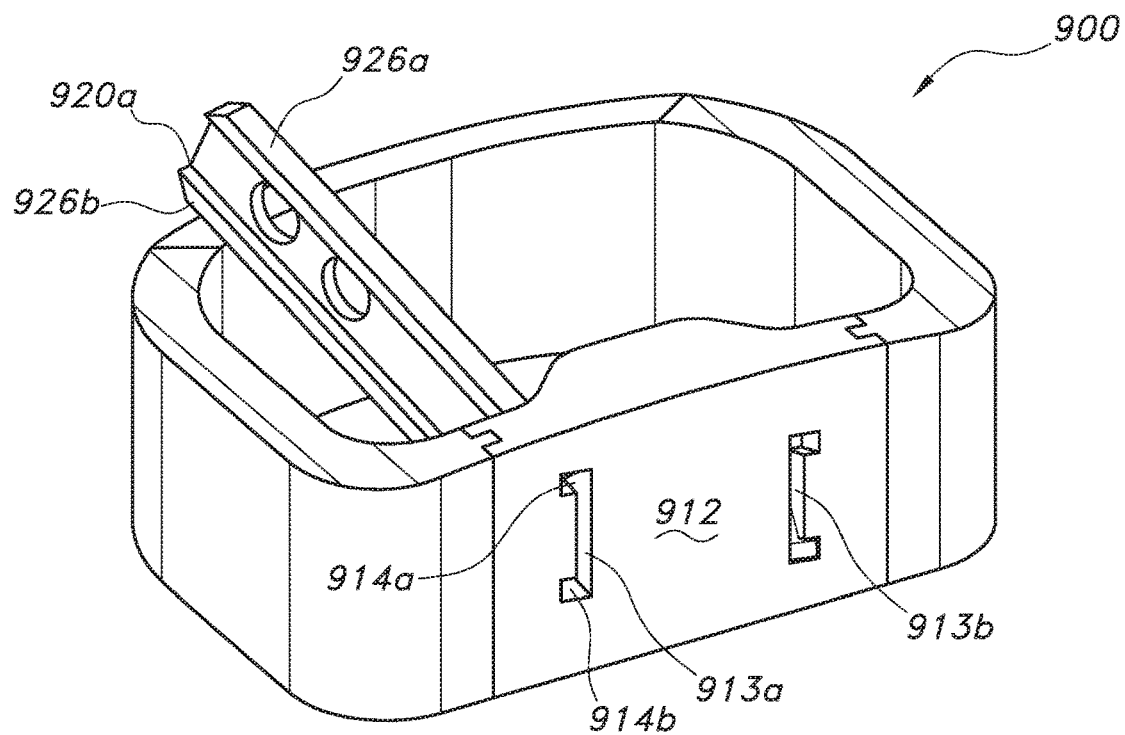
Figure 9D:
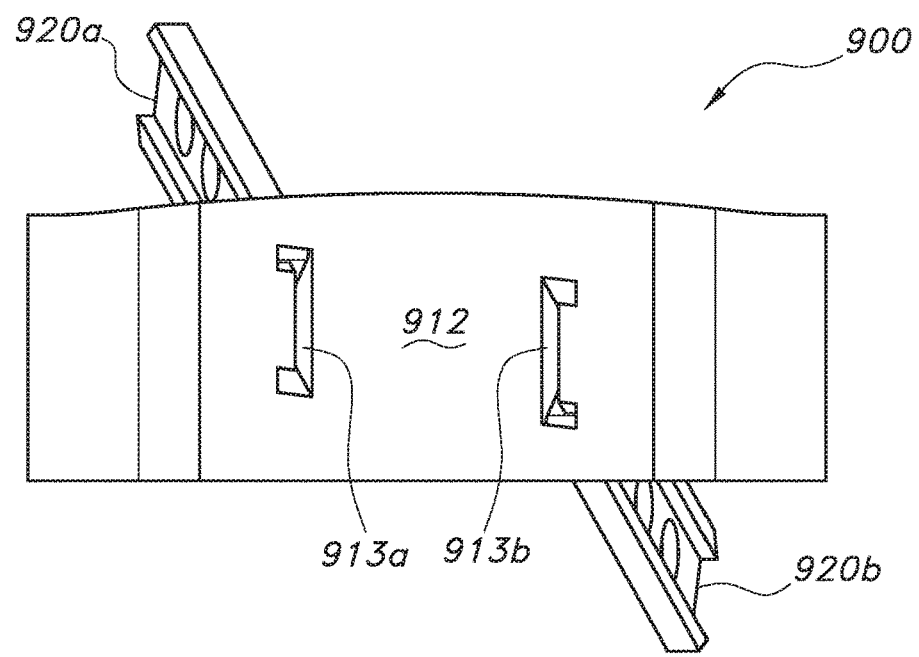

Preferably each keel contains a flange (926a and 926b) on each side of the blade 924, as shown in FIGS. 9C and 9D to prevent the keel (920a, 920b)) from sliding out of place after it is deployed in the patient. Each flange is generally perpendicular to the blade. Preferably the cross-section of the keel (i.e. blade and flanges) is in the shape of half of an I-beam, where an I-beam is split in half along a central longitudinal line (running along the length of the blade portion).

The keels have suitable dimensions to fit inside the cage and slide through the slots or cavities at an angle less than 90° relative to the superior or inferior surfaces of the cage. Suitable keels typically have widths ranging from about 1.5 to 3 mm and thicknesses ranging from about to 8 mm. The keels can be curved or straight.

(2.) Cage

The cage 10 contains an anterior wall (912). See, e.g., FIGS. 9A and 9B. In some embodiments the anterior wall is permanently affixed to the rest of the cage. In other embodiments the anterior wall is insertable into the cage. In either embodiment, the anterior wall is inserted into and attached to the cage prior to implantation in a patient.

The anterior wall 912 of the cage includes one or more slots (also referred to herein as cavities) (913a, 913b), typically two cavities (such as illustrated in FIGS. 9A-9D) into which a keel is inserted and through which the keel slides to reach its deployed position.

Each cavity contains two grooves (914a and 914b) that direct the keel in a downward or upward direction relative to the horizontal plane through the center of the cage at an angle suitable to allow the keel to exit the cage and extend into the proximal vertebral body. See, e.g. FIGS. 9C and 9D. For straight keels, the angle of each keel (and the groove that directs the keel) relative to the horizontal plane in the center of the cage is generally less than 90°. The shape of each cavity corresponds with the cross-section of the keel that is inserted therein. For example, as shown in FIGS. 9C and 9D, the cavity may have the shape of a half of an I-beam, with a long portion that corresponds with the length of the blade of the keel and two short portions at the top and bottom of the cavity, that correspond with the length of each of the flanges.

Optionally, the keels can be locked in place when in the deployed position. For example, the anterior wall (or front plate) could include a locking mechanism, such as illustrated in FIGS. 7A-7I.

(3.) Assembly and Implantation

After an anterior incision is made and the discectomy is completed, the cage is implanted into the disc space. Following implantation of the cage, the keels are inserted into each of the cavities, such that initially, each keel protrudes out the anterior wall of the cage, such as illustrated in FIGS. 9A and 9B. The keels are pushed through the anterior wall such that the tips of the keels pass through the inside of the cage, exit the cage and extend into the proximal superior and inferior vertebral bodies, respectively. FIGS. 9C and 9D show the location of the keels relative to the cage in the deployed position. When deployed, the keels extend into the proximal superior and inferior vertebral bodies for a sufficient distance to retain the cage in the disc space. Following implantation of the cage and the keels, the cage and the keels do not add to the anterior profile of the vertebral column.

ii. Deployed Using Gear

Figure 2A:
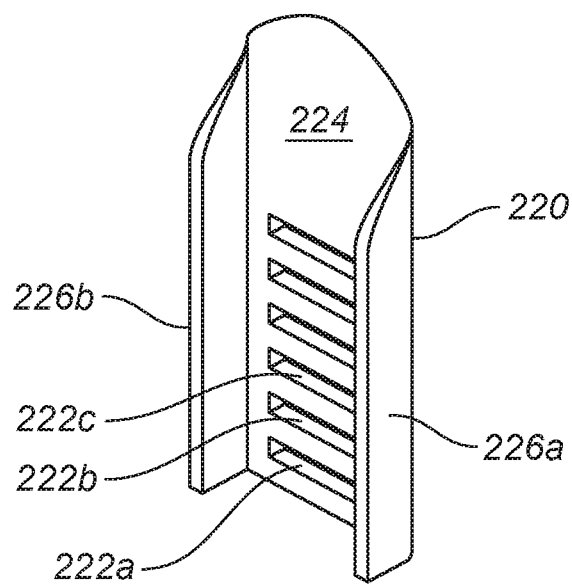
FIGS. 2A-2E are different views of an ALIF cage containing a deployable blade (also referred to as a keel).
Figure 2B:
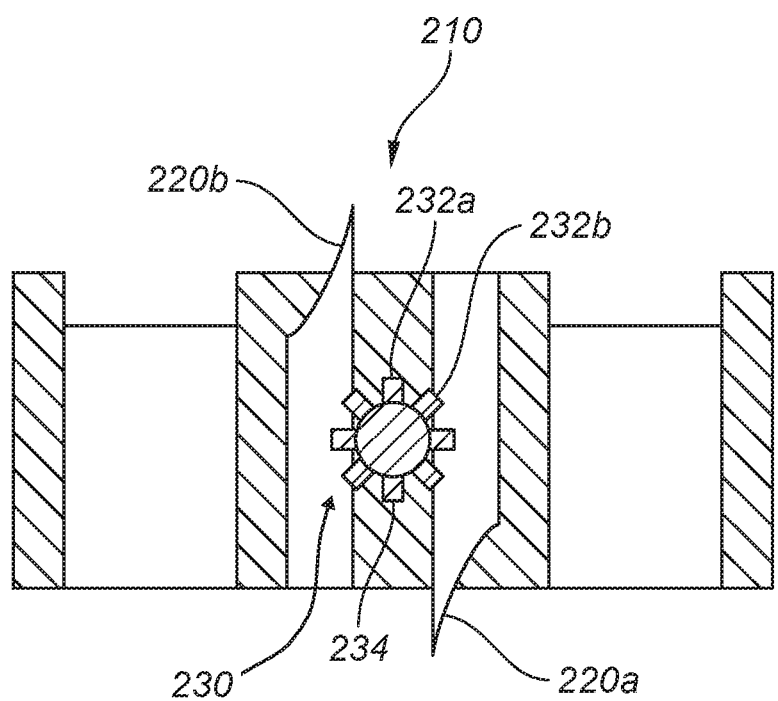
Figure 2C:
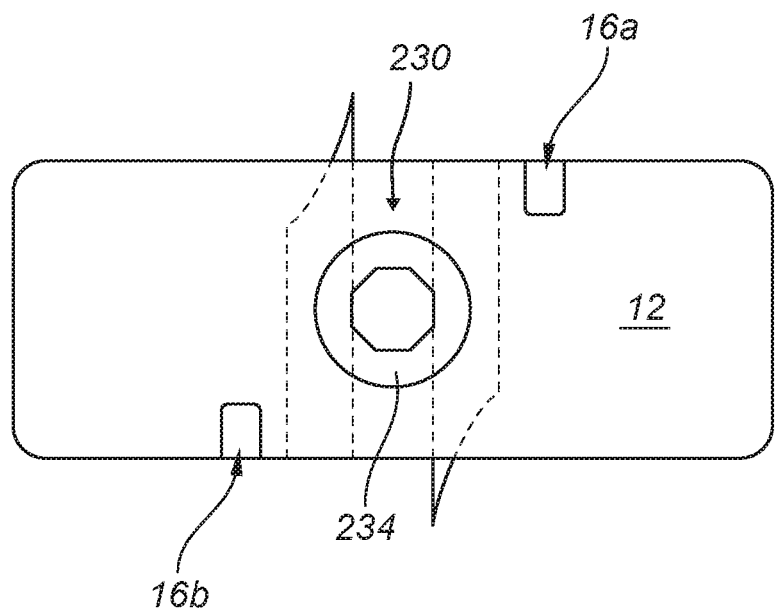
Figure 2D:
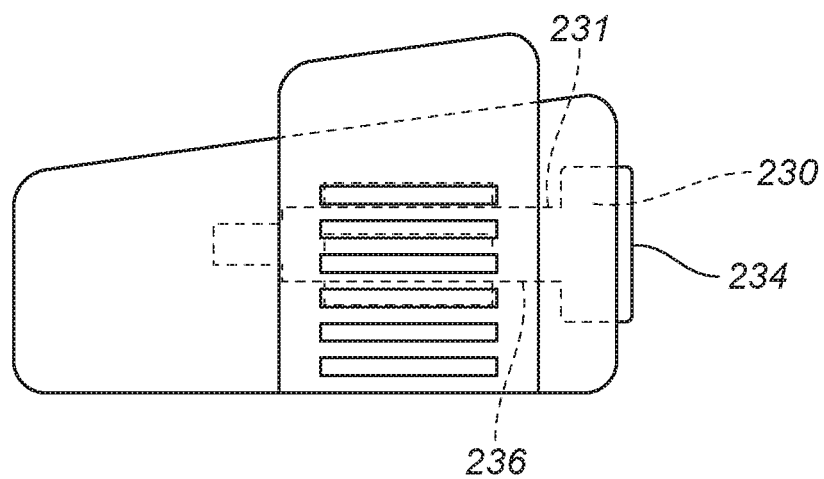
Figure 2E:
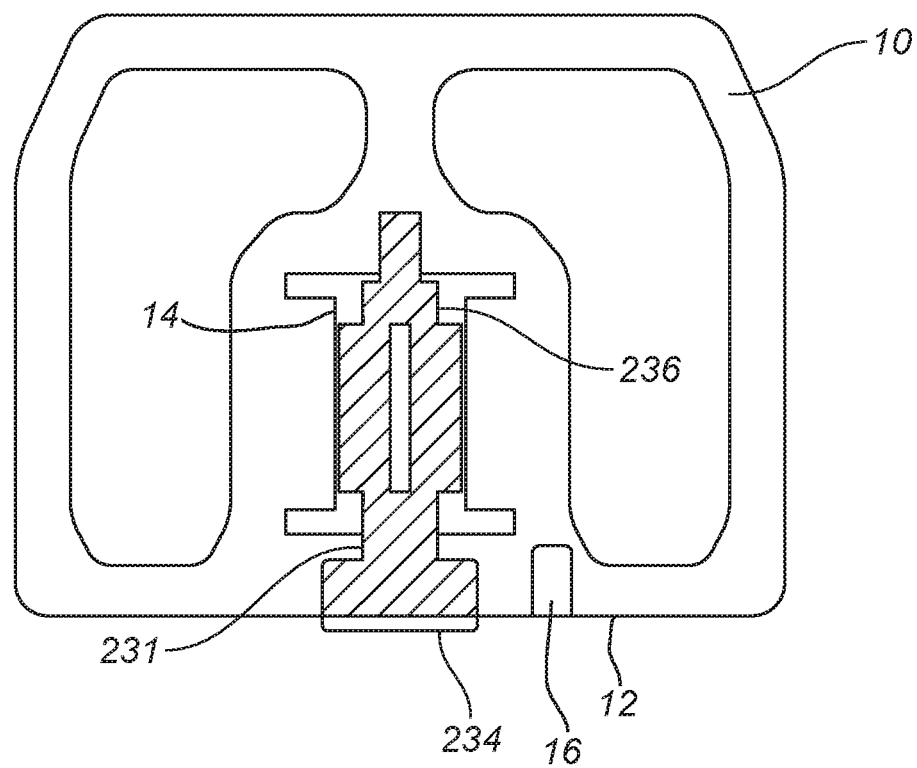

In another embodiment, illustrated in FIGS. 2A-2E, the fixation system 200 contains an intervertebral cage 210 with two deployable keels (220a and 220b). An exemplary keel 220 is shown in FIG. 2A. As shown in FIG. 2B, keels (220a, 220b) are connected to a gear mechanism 230, which is rotatable about an axis, forming a deployable keel device 210. In a preferred embodiment, the fixation system is preassembled with the deployable keel device 210 in the cage 10 prior to insertion in the patient, as shown in FIG. 2E.

In one embodiment, such as illustrated in FIGS. 2A-E, the keels may be inserted into the cage and deployed such that they extend in a substantially perpendicular direction relative to the cranial and caudal surfaces of the cage.

Figure 10A:
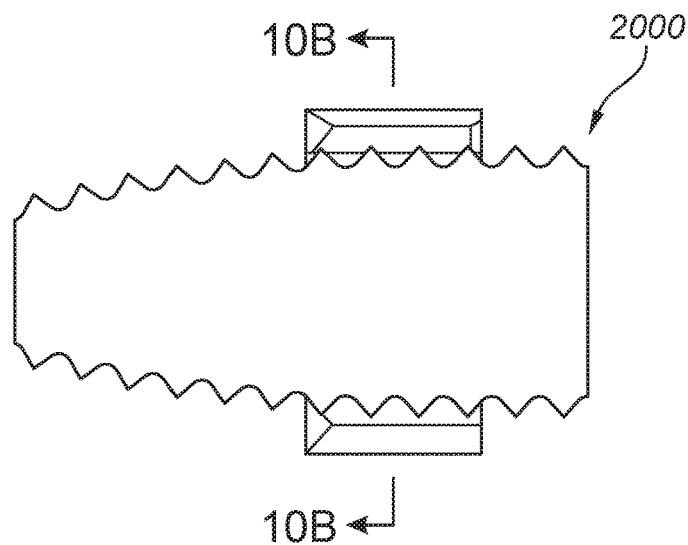
FIGS. 10A-10C are different views of an ALIF cage containing angled deployable blades (also referred to as keels).
Figure 10B:
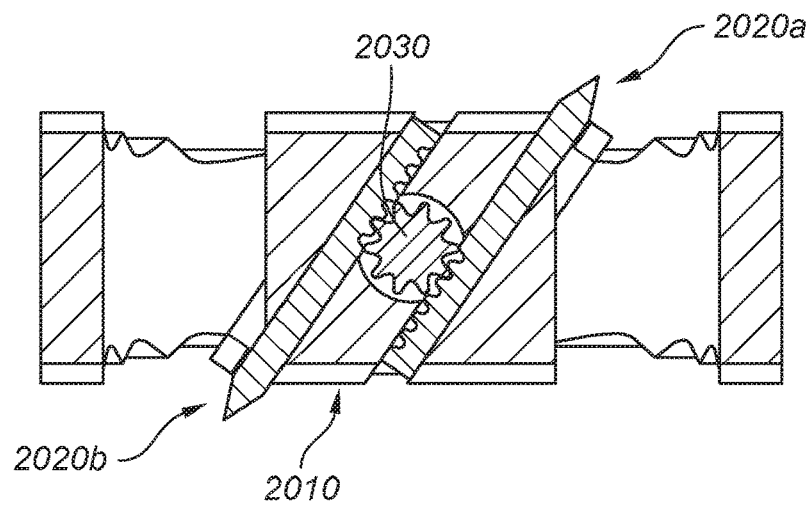
Figure 10C:
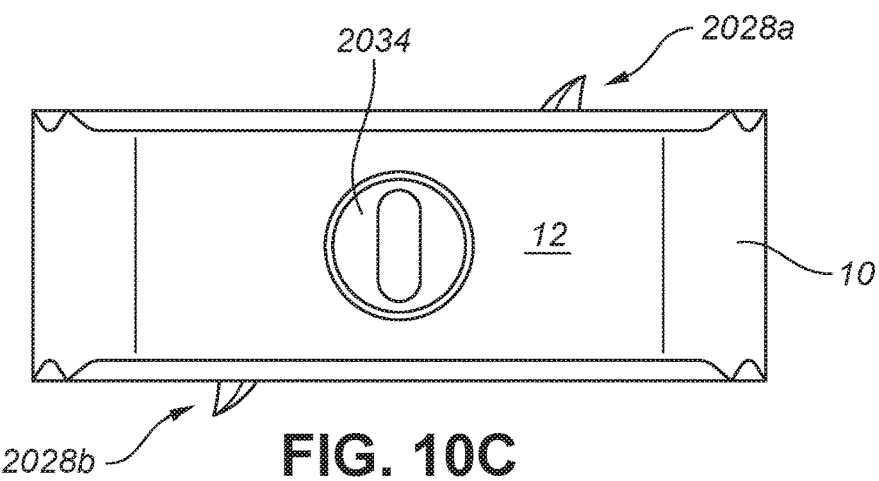

In another embodiment, such as illustrated in FIGS. 10A-C, the keels may be inserted into the cage and deployed such that they extend at an angle that is less than 90° relative to the cranial and caudal surfaces, preferably the keels extend at an approximately 45° angle. FIG. 10A illustrates an implant 2000. In this embodiment, due to the angled orientation of the keels, the length of each keel (2020a and 2020b) that is able to extend into the vertebral body is longer than the length of each keel (220a and 220b) that is able to extend into the vertebral body in the embodiment depicted in FIGS. 2A-E.

In one embodiment, the deployable keels, when in a retracted position, can fit within the cage. In another embodiment, the retracted keels have a partially protruding blade tip (2028a and 2028b), as shown in FIGS. 10A, 10b, and 10C. In this embodiment, the blade tips are proud of the cranial and caudal surfaces of the cage and cut a channel in the vertebral bodies upon insertion in the patient, which makes it easier to engage the blades when they are deployed.

(1.) Gear Mechanism

As shown in FIGS. 2A through 2E, 10B, and 10C, the gear mechanism (230 or 2030) contains a central screw (231; FIG. 2D) with small protrusions, e.g. teeth, (232a, b, etc.) around the circumference of the body 236 of the screw (see FIG. 2D). The gear mechanism has a sufficient size to fit inside the cage and rotate. Suitable diameters for the central screw range from about 4.5-6 mm, and suitable lengths range from about 8-11 mm. The central screw contains a head (234 or 2034) at its proximal end. Preferably the head contains means for turning the gear mechanism, e.g. a suitable shaped protrusion or depression to allow for an instrument to attach to the protrusion or depression and turn the gear mechanism. In a preferred embodiment, the head is a hexagonal screw head, as illustrated in FIG. 2C.

(2.) Keels

As illustrated in FIG. 2A, each keel 220 contains a plurality of slots (222a, b, c, etc.) along its blade portion 224, where the slots have a suitable size for each of the gear's teeth to fit inside a slot. Preferably each keel also contains a flange (226a, 226b) on each side of the blade 224 to prevent the keel from sliding out of place after it is deployed in the patient. Each flange is generally perpendicular to the blade. Preferably the cross-section of the keel (i.e. blade and flanges) is in the shape of half of an I-beam, where the I-beam is effectively split in half along a central longitudinal line (running along the length of the blade portion).

The keels have suitable dimensions to fit inside the cage and slide upward or downward, optionally at an angle less than 90° relative to the superior or inferior surfaces of the cage, when the gear mechanism is rotated. Suitable keels may have widths ranging from about 1.5 to 3 mm and thicknesses ranging from about to 8 mm.

Typically, one keel is located on each side of the gear mechanism, as shown, for example, in FIG. 2B.

(3.) Cage

The cage 10 contains a screw shaft 14, which is formed of a bore having a size and shape suitable for the gear mechanism to fit inside the shaft and deploy the keels. The anterior face 12 of the cage contains bore having a suitable diameter for the body of the head of the screw to fit inside the bore. Preferably the cage also contains one or more, preferably two, slots 16 for attachment to an insertion tool to facilitate insertion of the cage into the patient's spine at the desired location.

Additionally, the cage contains a front plate, which is preassembled to the cage.

(4.) Assembly and Implantation

After an anterior incision is made and the discectomy is completed, the cage is implanted into the disc space. At the time of implantation, as shown in FIGS. 2C and 10C, the head (234 or 2034) of the gear mechanism (230 or 2030) extends slightly beyond the anterior face 12 of the cage 10. Initially, at least one of the teeth is inserted into and connects with one of the slots. When the gear mechanism (230 or 2030) is rotated, typically in a clockwise direction, the tooth that is inserted into a slot, pushes the slot downward or upward and exits the slot, simultaneously the proximal tooth is inserted into the proximal slot. This continues as the gear mechanism is rotated, which pushes one keel in a generally upward direction and the other keel in a generally downward direction, optionally at an angle less than 90° relative to the superior or inferior surfaces of the cage, until the keels are in their deployed or extended state. In the extended state, each of the keels protrudes past the superior or inferior surface of the cage by about 3 mm to about 6 mm.

Optionally a front metal plate is placed over and attached to the anterior face of the cage to fix the screw of the gear mechanism in place and prevent it from inadvertently rotating following deployment of the keels.

3. Outer Plate with Keel(s)

Figure 3A:
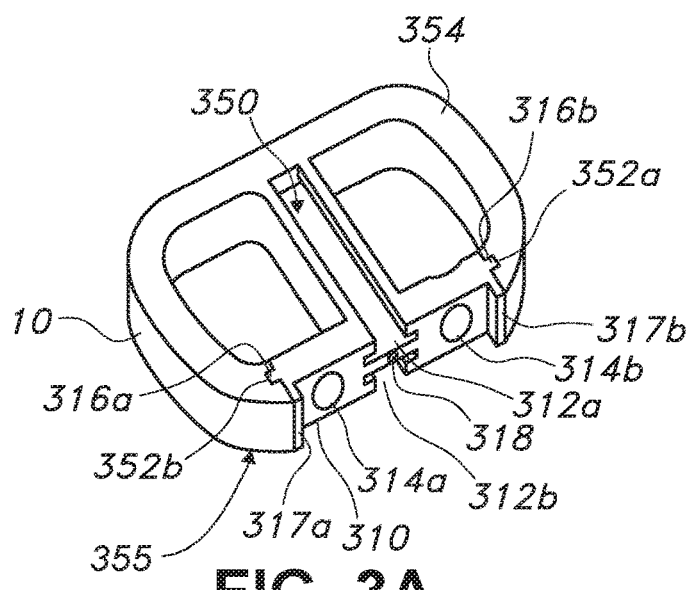
FIGS. 3A-3D are different views of an ALIF cage with a front (outer) plate containing two blades (also referred to as keels).
Figure 3B:
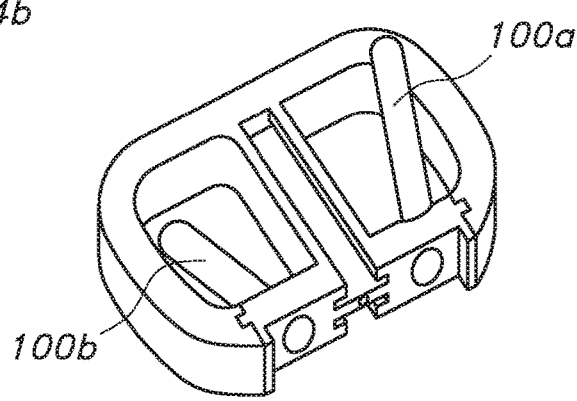

In one embodiment, such as illustrated in FIGS. 3A-3D, the fixation system 300 contains an intervertebral cage 10, an inner plate 310, and an outer plate, also referred to as a front plate 340. Optionally, the system includes additional fixation elements, such as one or more screws or fluted nails (100a and 100b), as shown in FIG. 3B.

a. Inner Plate

The inner plate affixes directly to the anterior side of the intervertebral cage. The inner plate also typically contains one or more, preferably two, holes (314a and 314b), as shown in FIG. 3A, for receiving a fixation element, such as a screw or a fluted nail. Preferably the cross-section of the hole mates with the cross-section of the screw or nail.

Any suitable means for affixing the inner plate to the intervertebral cage can be used. As illustrated in FIG. 3A, the inner plate may contain an extension portion (316a and 316b) on each side (317a and 317b) of the plate. Each extension portion extends beyond the outer face of the side of the plate and has a suitable size to fit in slidable relation to a slot (352a and 352b) in the cage 10.

The inner plate also includes channels 350 defining a first slot 312a on the superior side of the plate and a second slot 312b on the inferior side of the plate. These slots have a size and shape suitable for receiving the bottom portion of a keel. In a preferred embodiment, the slot has a T-shaped cross-section.

Preferably the inner plate contains a central bore 318 having a suitable size and shape for receiving a locking screw.

Any suitably strong, biocompatible and inert material can be used for the inner plate. In a preferred embodiment, the inner plate is formed from titanium.

b. Outer Plate

Figure 3C:
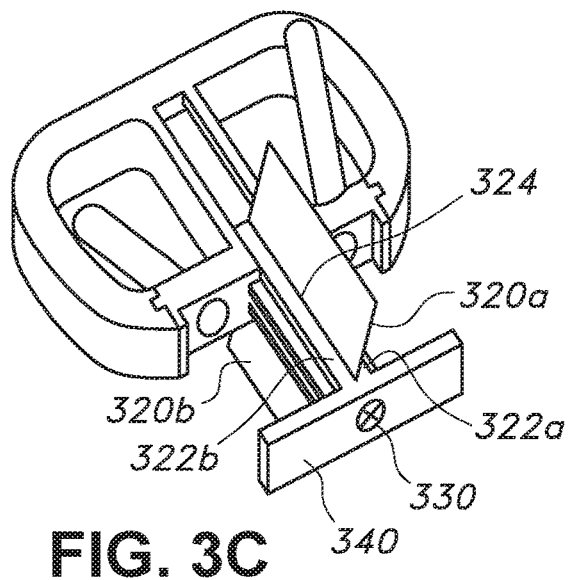
Figure 3D:
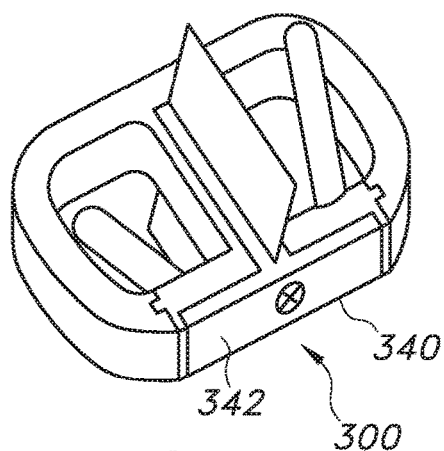

The outer plate 340 contains a top keel 320a and a bottom keel 320b, as shown in FIG. 3C. As shown in FIG. 3B, the top and bottom keels have a keel attachment portion 324 with a size and shape that is suitable for slidable insertion into a first slot 312a in the superior portion of cage 10 and second slot 312b in the inferior portion of the cage 10.

The outer plate also contains at least one bore (not shown) having a size and shape suitable for receiving a locking means preferably a screw 330, which can be turned to lock the outer plate in place following insertion into the cage. (see, e.g. FIGS. 3C and 3D). Preferably the bore is threaded to mate with the threads on the locking screw.

The outer plate can also serve as a locking means for the keels by preventing the keels from sliding out of position.

Preferably the outer plate has a suitable size and shape, optionally a rectangular shape as illustrated in FIG. 3C to cover the inner plate. In this embodiment, the outer plate serves as a front plate, which locks the inner plate in place so that it remains affixed to the anterior side of the intervertebral cage.

c. Cage

As shown in FIG. 3A, cage 10 contains channels 350 defining a first slot 312a on the superior side 354 of the cage 10 and a second slot 312b on the inferior side 355 of the cage 10. These slots have a size and shape suitable for receiving the bottom portion of a keel. In the preferred embodiment, the slots have a T-shaped cross-section.

The cage 10 preferably contains a bore having a size and shape suitable for receiving a locking means preferably a screw 330.

d. Assembly and Implantation

Prior to insertion in a patient's body, the inner plate is assembled with the cage, such as by sliding the extension portions (316a and 316b) in the slots (352a and 352b) to attach the inner plate to the anterior portion of the cage, as shown in FIGS. 3A through 3D. After the discectomy is completed, the cage is implanted into the disc space between the vertebral bodies in a patient. Preferably following insertion of the cage, the cage is fixed in place using one or more fixation elements, such as by inserting screws or fluted nails into the one or more, preferably two, holes (314a and 314b) in the inner plate. Then the keels are attached to the cage by sliding the keel attachment portion in the channel (350) in each of the superior (354) and inferior (not shown) outer surfaces of the cage. Finally the outer plate is locked in place by inserting a locking screw into the bore in the outer plate and rotating the screw until it is flush with the anterior surface (342) of the outer plate (see FIG. 3D).

4. Keels Attachable to the Cage

In one embodiment, the cage contains a first channel, such as a "T" channel, on the anterior surface and a second channel on the inferior surface, such as illustrated in FIG. 3A, as described above. The size and shape of the channels are suitable for insertion of a keel into each of the top and bottom surfaces.

Instead of using keels that are integral with an outer plate, the keels can be separate from the outer plate. Each keel can slide into one of the channels of the cage. Then a front plate, optionally with one or more holes for fixation elements, such as screws or fluted nails, can be affixed to the anterior portion of the cage. Further the plate has a suitable size and shape to cover at least the keel attachment portion of each of the keels and thereby lock the keels in place. The front plate is locked in place by inserting a locking screw into the bore in the outer plate and rotating the screw until it is flush with the anterior surface (342) of the outer plate.

In alternative embodiments, the keels can be moved into the desired position through slots in the anterior portion of the cage or anterior plate and then deform or bend so that the keels lock in place. An exemplary embodiment of a locking blade and corresponding slots or cavities in the cage is illustrated in FIGS. 7A-7I.

5. I-Beam Fixation

In one embodiment the intervertebral cage is stabilized by two keels that cross each other when placed inside the cage and the anterior ends of the keels are able to lock in the desired location, such as by interlocking with each other to form an I-beam, or by other suitable locking means. For example, one end (the proximal end) may be located in or attached to two portions that interlock to form an I-beam attachment portion. Preferably this embodiment does not require a front plate to attach the keels and lock them in place. The flanges in the I-beam attachment portion preferably form a dove tail joint in the cage, preferably in the anterior region of the cage, to prevent its removal (pullout) from the cage.

In one embodiment, the cross section of each keel's blade forms half of an I-beam attachment portion. At least one of the blades contains grooves that allow the second blade to mate with and interlock with the first blade when the blades are placed inside the cage. Once assembled, the interlocked blades resist rotation of the cage and the I-beam formed at the anterior end of the assembly resists flexion/extension and pullout/translation of the cage.

FIGS. 4A-4F illustrate one embodiment of a device that utilizes I-beam fixation. As shown in FIG. 4D, the device contains an intervertebral cage 10 and an I-beam fixation system 400, which preferably contains a first half I-beam portion 410a and a second half I-beam portion 410b, and at least one keel, preferably two keels (420a and 420b), as shown for example in FIG. 4B.

a. Half I-Beam Portions

As shown in FIGS. 4A, 4E, and 4F, the first half I-beam portion 410a and the second half I-beam portion 410b mate to form an I-beam attachment portion 430 which is insertable in slidable relation to the slots (452a and 452b) in the anterior portion 456 of the cage 10.

Each half I-beam portion contains an extension portion (412a, 412b) on one side 411, where the extension portion has a size and shape suitable for slidably inserting it into the first and second slots (452a and 452b) in the cage 10.

As shown in FIG. 4F, each half I-beam portion also contains a cavity 413 for receiving the keel, which optionally contains one or more grooves (414a and 414b), typically two grooves on the side of the half I-beam portion that is opposite the extension portion. The cavity has a suitable shape and size to receive one of the keels. Each groove is a depression that has a suitable shape and depth for receiving the flange on the blade of the keel. In a preferred embodiment, in one half I-beam portion, the grooves are angled downward to direct the keels to the inferior vertebral body, while in the other half I-beam portion, the grooves are angled upward to direct the keel to the superior vertebral body.

b. Keels

As shown in FIGS. 4B and 4C, the keels may have a keel attachment portion (422a and 422b) with a size and shape that is suitable for insertion into a depression (450a, 450b) in the anterior portion of the cage 10.

The keel also contains a blade portion (424a, 424b or 460a, 460b) having a suitable shape and size. The blade portion is oriented to extend the tip 428 of the blade portion beyond the superior surface 458 or inferior surface of the cage when the fixation system 400 is assembled, such that the tip of the blade portion enters and extends into the proximal vertebral body. Preferably the blade portion is curved to facilitate placement in the proximal vertebral body (see FIG. 4B). In an alternative embodiment, the blade portion may be straight (see FIG. 4C).

Preferably each keel also contains a flange (426a, 426b or 466a, 466b) on each side of the blade (424a, 424b or 460a, 460b) to prevent the keel from sliding out of place after it is deployed in the patient. Preferably the cross-section of the keel (i.e. blade with flanges) is in the shape of half of an I-beam.

c. Cage

As shown in FIG. 4A, cage 10 contains an open region 454 in the center of the anterior portion 456 of the cage. The open region contains a first slot 452a and a second slot 452b on the right and left sides of the anterior portion of the cage. In one embodiment, the slots have a size and shape suitable for receiving the extension portions (412a and 412b) of the I-beam attachment portion 430. In a preferred embodiment, the slot has a T-shaped cross-section.

The cage 10 preferably contains a depressed area (450a and 450b) on each side surrounding the opening 454 in the anterior portion of the cage. The depressed area has a size and shape suitable for receiving a locking means, preferably formed by the keel attachment portion in proximal end of the keel.

In an alternative embodiment, the slots contain one or more locking means which are configured to deform the proximal portions of each keel (See FIGS. 7A-E).

d. Assembly and Implantation

Prior to insertion in a patient's body, the I-beam attachment portion 430 is assembled and inserted into the cage, such as by sliding the extension portions (412a and 412b) in the slots (452a and 452b) to attach the I-beam attachment portion to the anterior portion of the cage. After the discectomy is completed, the cage is implanted into the disc space between the vertebral bodies in a patient. Preferably following insertion of the cage, the cage is fixed in place using one or more fixation elements, such as by inserting one or more, keels into the cage by sliding one keel along the grooves (414a and 414b) and through the opening 432 in the I-beam attachment portion and sliding a second keel along the grooves (414c and 414d) and through the opening 432 in the I-beam attachment portion until their proximal portions (422a and 422b) are adjacent to the depressed portions (450a and 450b) of the cage. (See FIGS. 4A-4F.)

In some embodiments, the cage does not contain depressed portions. Rather, optionally, each slot contains one or more locking means configured to deform the proximal portion of each keel so that the keel locks in place.

6. Locking Mechanism

Figure 5A:
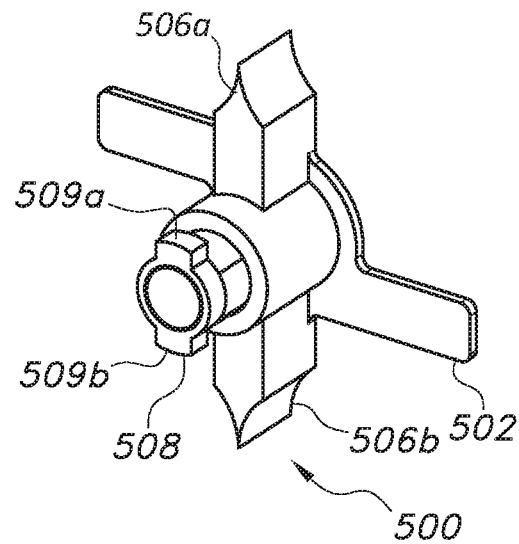
FIGS. 5A-5D are different views of the ALIF cage with locking element for two screws or fluted nails.

Optionally, two or more additional fixation elements, such as screws, fluted nails or pins can be inserted into the cage to prevent the fixation elements from moving out of their intended location using a suitable locking mechanism 500, as shown in FIG. 5A. The locking mechanism is formed from a biocompatible, non-degradable material, with sufficient strength. Suitable materials include but are not limited to stainless steel and titanium.

Figure 5B:
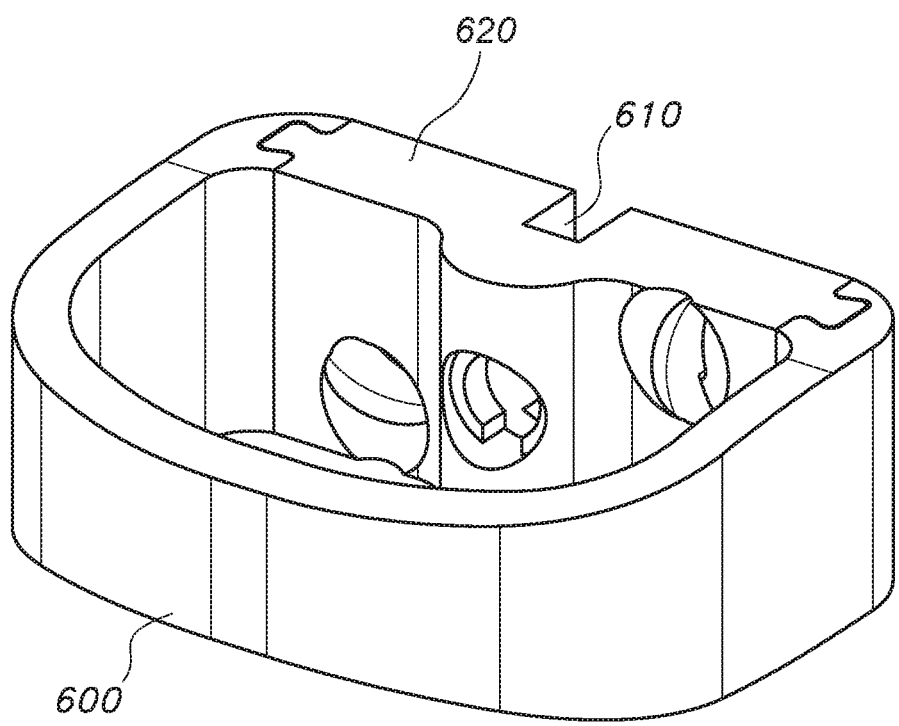
Figure 5C:
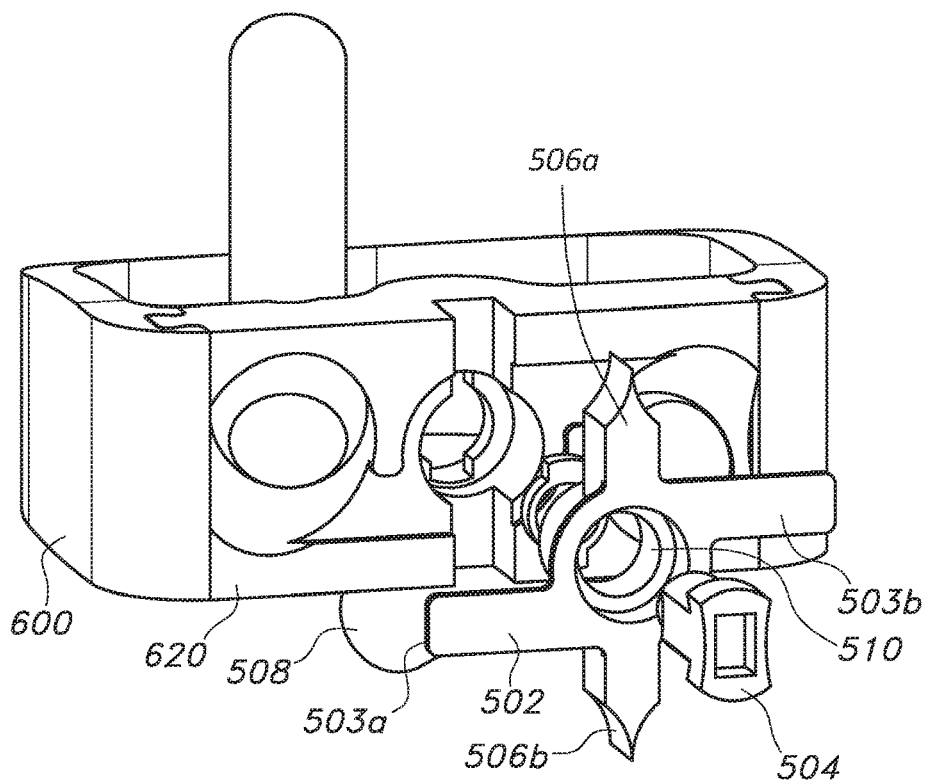
Figure 5D:
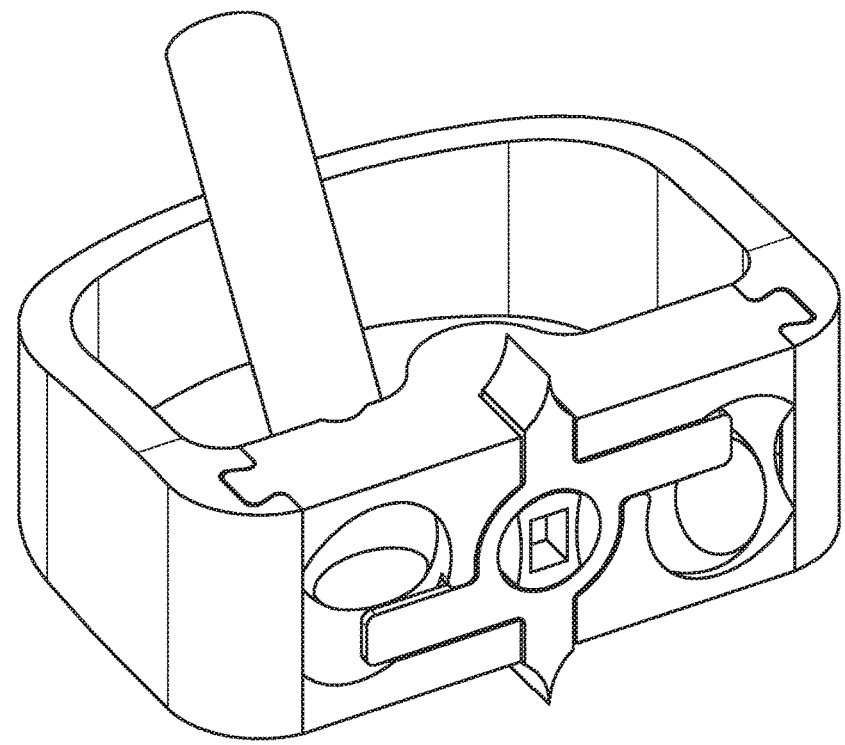
Figure 6A:
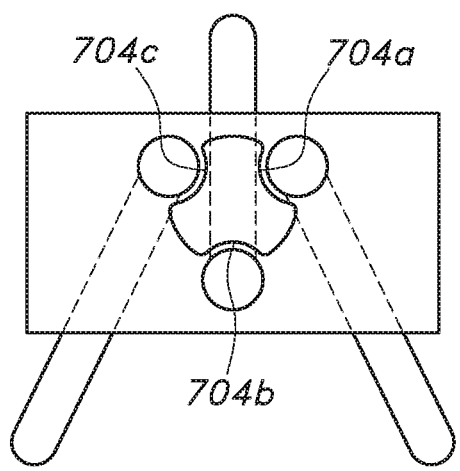
FIGS. 6A-6C are illustrations of different locking elements.
Figure 6B:
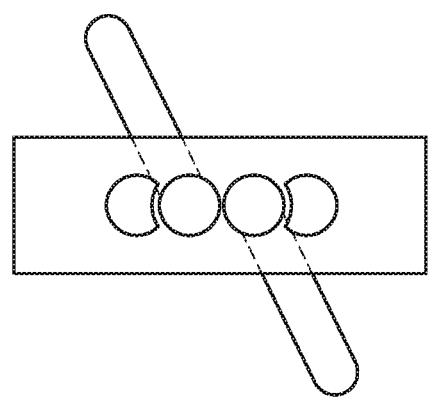
Figure 6C:
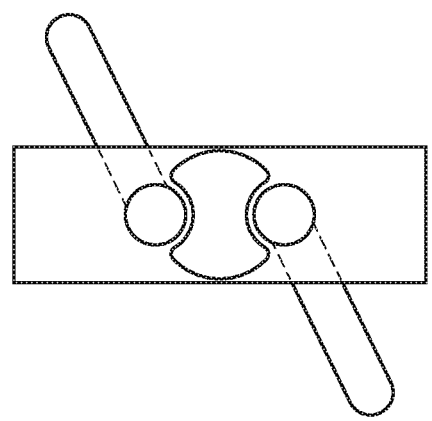

The locking mechanism is typically attached to the front plate or the anterior portion of the cage 600 shown in FIG. 5B, via a connection element. Typically, the front plate contains a hole 610 into which a mating connection element in the locking mechanism fits. The anterior face 502 of the locking mechanism has a suitable size and shape to cover in whole or in part the heads of the two or more fluted nails or other fixation elements. A representative shape is illustrated in FIG. 5C, which contains two horizontal, extension portions (503a and 503b) that partially cover two fixation elements. Alternative embodiments and shapes are illustrated in FIGS. 6A-6C. In one embodiment, the locking mechanism is in the shape of a figure eight (see FIG. 6B) or a circle if only two fixation elements are covered. In another embodiment for covering three fixation elements, the locking mechanism is in the shape of a circle with a sufficient diameter to cover at least a portion, or all, of the head portion of the fixation elements.

Another representative shape for the locking mechanism is illustrated in FIG. 6A as a circle with open portions (704a, 704b, 704c), typically equally spaced about the circumference of the circle. Preferably the head has three openings. The open portions are of a suitable size to allow a fluted nail, including the head of the nail, to pass through. In the unlocked position, the open portions align with the bores in the front plate. Then the fluted nails or other fixation elements are inserted through each open portion and into the corresponding bore until the head of the nail or other fixation element is substantially flush with the surface of the front plate and is below the head of the locking mechanism. Then the locking mechanism is turned, if necessary using a suitable device, until the head of the locking mechanism covers all or a portion of each of the fixation elements. This position corresponds with the locked position.

Optionally, the locking mechanism contains multiple components. An exemplary embodiment is illustrated in FIGS. 5A-5D. In this embodiment, the locking mechanism 500, contains a front locking portion 504, a plate 502 having a suitable size and shape to cover in whole or in part the heads of the two or more fluted nails or other fixation elements, optionally with one or more keels (506a and 506b), and a back locking element 508. As shown in FIG. 5C, the front locking portion contains two horizontal, extension portions (504a and 504b) that partially cover two fixation elements. The keels (506a and 506b) are integral with the front locking portion and extend in a generally perpendicular direction relative to the extension portions, with one keel extending in the superior direction and the second extending in the inferior direction. The front locking portion also contains a central bore 510 having a size and shape suitable for mating with the front and back locking elements. The front locking element has a smaller diameter and fits inside the central bore. The back locking element has a central hole with a diameter that is slightly greater than the diameter of the front locking portion such that the back locking element fits over the posterior portion of the front locking element. The back locking portion also contains two flanges (509a and 509b), as shown in FIG. 5A.

Prior to insertion, the ALIF cage and the front plate 620 are assembled, as shown in FIG. 5C. The cage is then inserted between the two vertebrae in need of treatment. Then the fixation elements, such as fluted nails or screws, are inserted through the holes in the front plate until the head of the fixation element is essentially flush with the anterior face of the front plate. The locking mechanism is preassembled and then inserted into a central bore in the front plate. After insertion, the locking mechanism is locked in place by rotating the head of the front locking portion. This rotation also rotates that back locking element such that the flanges extend beyond the diameter of the central bore, preventing accidental pull out from the front plate/cage assembly. When fully assembled, the extension elements on the front locking portion 504 partially or fully cover each head of the fixation elements, thereby preventing their accidental removal, or pull out from the front plate/cage assembly.

In one embodiment, the locking mechanism can be formed when a portion of the keels contacts or passes a region of the cavity or slot in the I-beam housing or cage. Preferably one or more locking elements are located in a cavity in the anterior portion or wall of the device, more preferably in an I-beam attachment portion or in a cavity in the anterior wall (or attachment portion) of the cage.

Figure 7A:
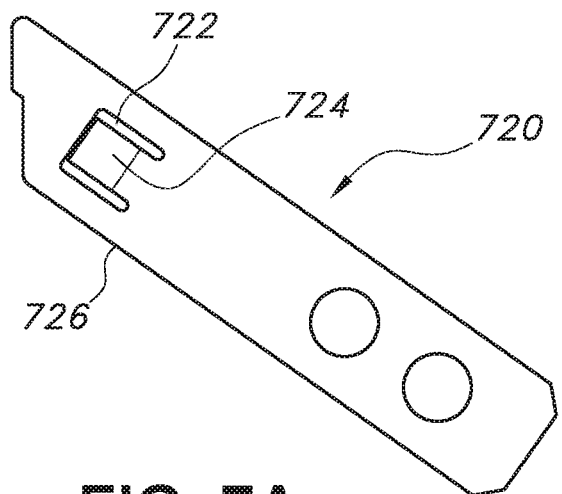
FIGS. 7A-H are illustrations of an embodiment for locking a keel in a desired position within a cage using a locking tab.
Figure 7B:
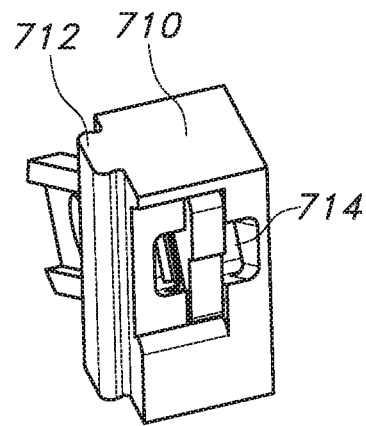
Figure 7D:
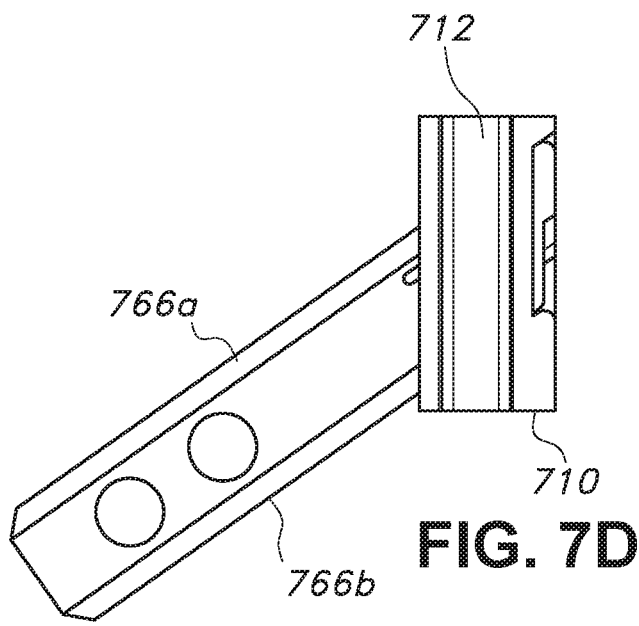
Figure 7C:
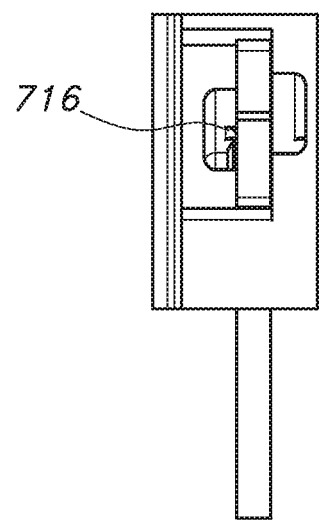
Figure 7E:
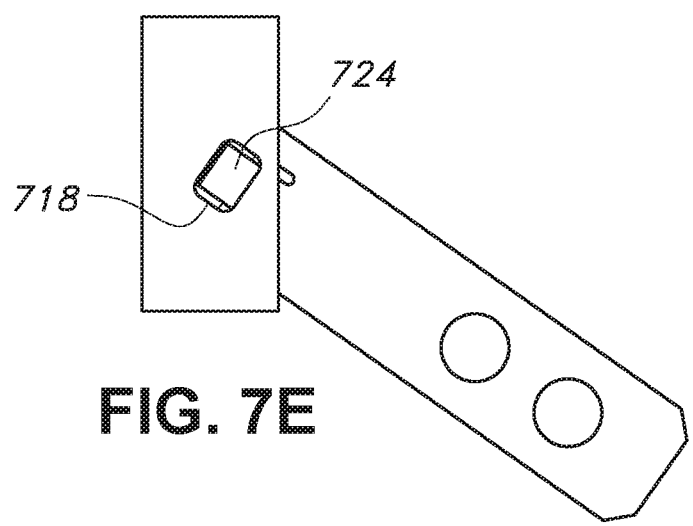

For example, as illustrated in FIG. 7A, each keel 720 may contain a U-shaped channel 722 at its proximal end 726 which defines a deformable tab 724. The tab in the center of the U-shaped channel is shown in its initial, unlocked position. The tab 724 can be deformed into a locked position, and can later be returned to its initial, unlocked position.

As illustrated in FIGS. 7B-7E, the half I-beam attachment portion 710 contains a cavity 714 configured to receive the keel so that it can slide though the cavity into a deployed position. One side of the cavity contains a protrusion 716 configured to push the tab when the keel slides through the cavity. The opposite side of the cavity contains an opening 718 configured to receive the tab, when it is pushed and deformed by the protrusion.

Figure 7F:
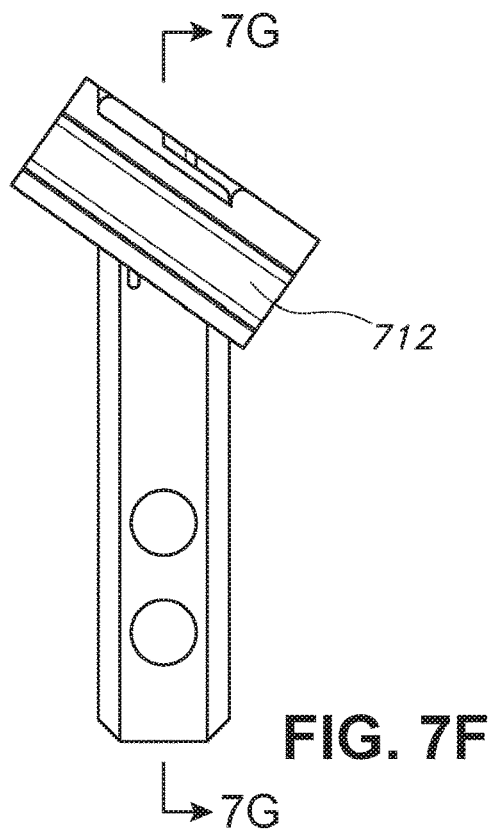
Figure 7G:
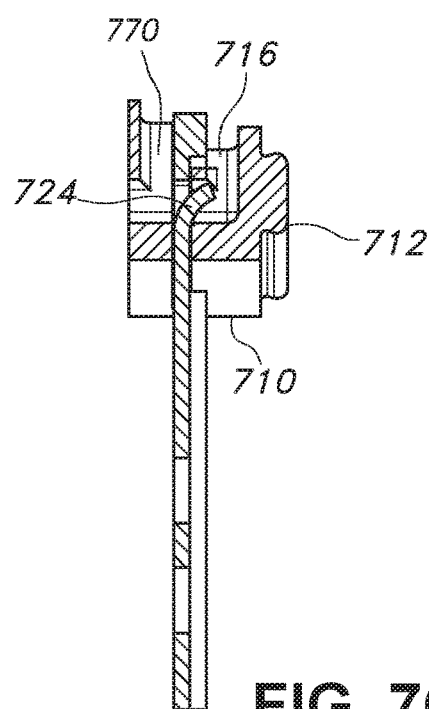

As the proximal portion 726 of the keel slides through the cavity past the protusion 716, the protrusion pushes the tab 724 into the opening 718. This locks the keel into the deployed position. FIGS. 7F and 7G illustrate the keel in the locked position within the half I-beam attachment portion 710. Once the keel reaches the deployed position, the locking tab is deformed to the locked position preventing mobility of the keel. This locking mechanism prevents the keel from sliding forward or backward. Optionally, an instrument is inserted in a first cavity (labeled "770" on FIG. 7G) and pushes the tab into a bent or locked position.

Figure 7H:
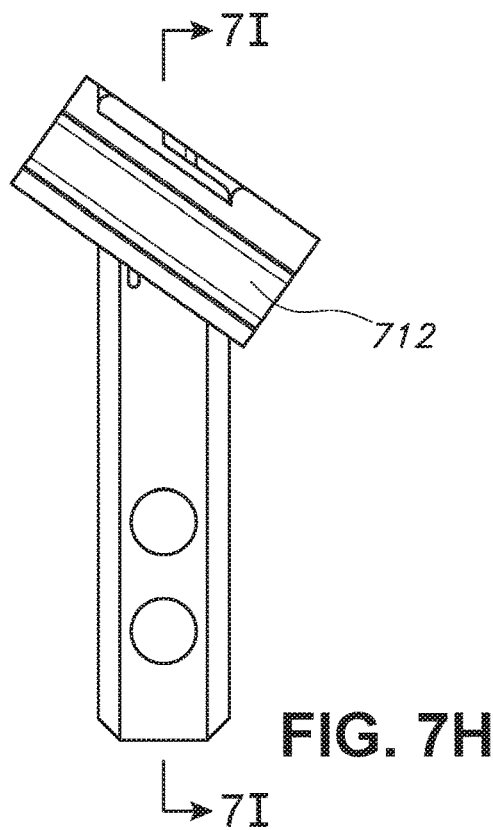
Figure 7I:
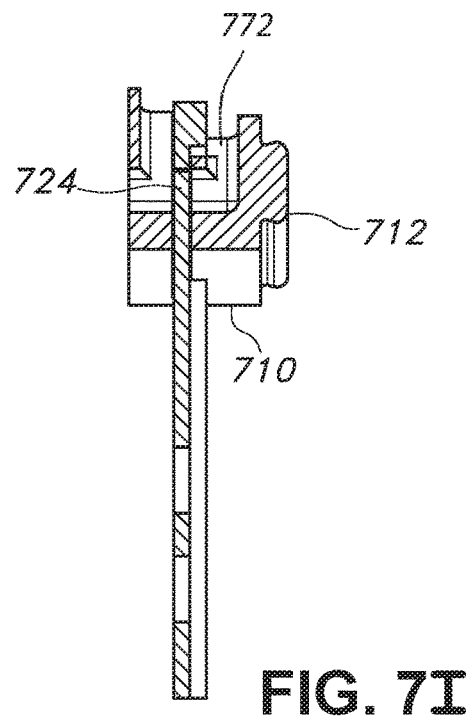
Figure 8A:
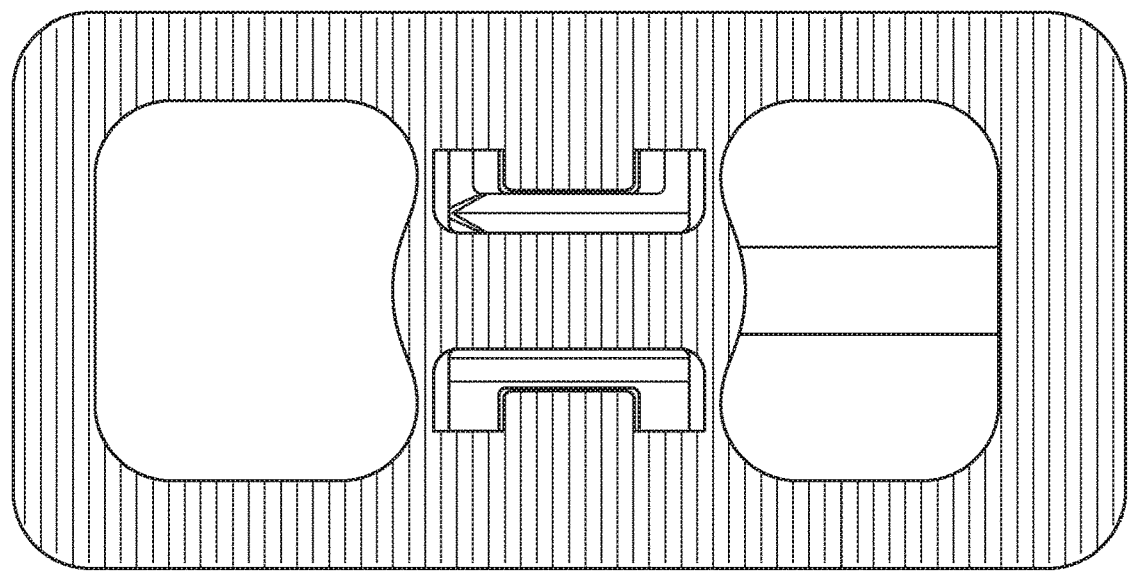
FIGS. 8A-8C are illustrations of an exemplary system for lateral approach during a lumbar intervertebral fusion.
Figure 8B:
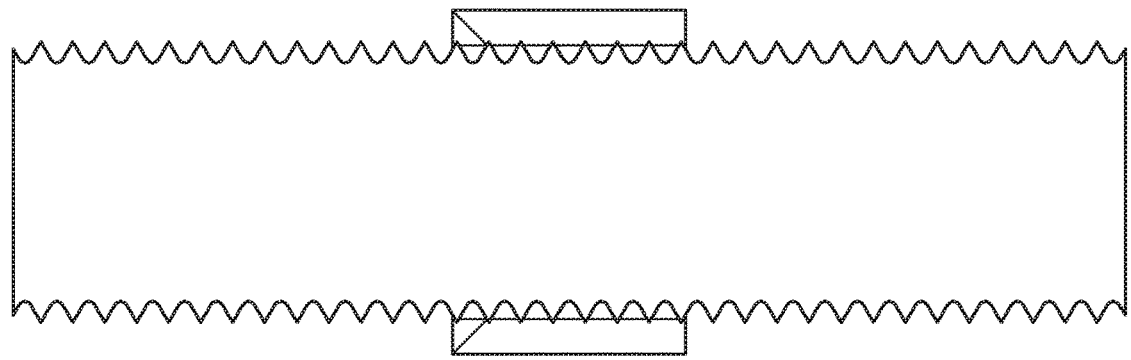
Figure 8C:
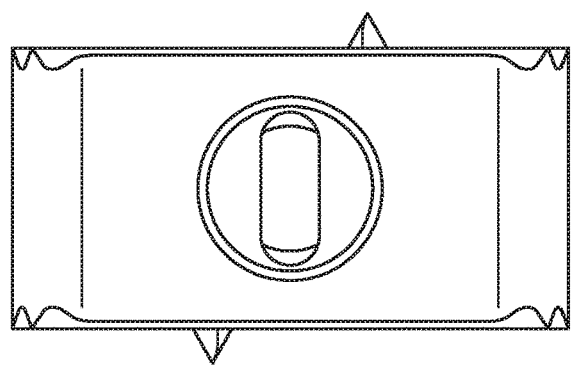

FIGS. 7H and 7I illustrate the keel in the unlocked position within the half I-beam attachment portion (710). For example, a suitable tool or instrument can be inserted into a second cavity (labeled "772" on FIG. 7I) and pushes the tab to bend the tab back to its initial, unbent state (i.e. the unlocked position).

II. Kits Containing the Device

The fixation device may be provided as part of a kit for an ALIF, anterior cervical fusion or lateral interbody fusion (LIF). The kit may contain an intervertebral cage and at least one fixation device. Preferably the kits contains one or more keels, typically it contains at least two keels. Preferably, the kit contains one or more fluted nails, more preferably at least two fluted nails. In some embodiments, the kit contains three fluted nails, optionally more. The kit also contains instructions for care and insertion of the spinal fixation system.

In some instances it may not be clear what size or shape keels are needed until the surgery has begun. Having a kit that provides several options allows for the device to be altered based on unforeseen circumstances or anatomical circumstances. The kit may provide a modular fixation device, with one or more different intervertebral cages, optionally different sized cages, more than one different sized and shaped keels and more than one type of attachment portion. The attachment portions may be an anterior wall configured to attach to the rest of an intervertebral cage, two half I-beam portions configured to attach to an intervertebral cage to complete the anterior portion of the cage, or a front plate, optionally with a back plate. Optionally, multiple anterior walls are provided containing different angles for the two cavities and/or different shaped cavities, where some are configured to receive straight keels and others are configured to receive curved keels.

In another embodiment, optionally the kit contains different half I-beam portions containing different locking means.

The kit can include curved and/or straight keels and/or keels of different sizes. This allows for each device to be assembled as needed on site. The practitioner can select the appropriate keels for the individual patient.

In one embodiment, more than one cage is provided in the kit. A cage specific for angled keels and a cage specific for keels that are perpendicular to the bone can be supplied. In some instances, a cage that allows for the keels to protrude out the anterior wall is also provided. Because different keels can be used for each of the different cages, a variety of keels can also be provided in the kits.

In one embodiment, the kit can contain preassembled cages.

The kit may also include tool(s) for placement of the cage and fixation device. In one embodiment, the kit can include tools and materials for inserting bone graft material. For example, the kit can include a syringe or other apparatus for injecting bone graft material.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. An intervertebral cage implant, comprising:
a cage configured to be implanted between two vertebrae;
a first deployable keel, including a first blade, a first flange extending substantially perpendicularly from a first edge of the first blade, and a second flange extending substantially perpendicularly from a second edge of the first blade, such that the cross-section of the first deployable keel is in the shape of half of an I-beam;
a second deployable keel, including a second blade, a third flange extending substantially perpendicularly from a first edge of the second blade, and a fourth flange extending substantially perpendicularly from a second edge of the second blade, such that the cross-section of the second deployable keel is in the shape of half of an I-beam;
wherein a first portion of the first keel is configured to fit inside the cage in a first retracted position and deploy from the cage in a generally superior direction to a first extended position in which the first portion of the first keel is disposed superior to the cage of the implant;
wherein a second portion of the second keel is configured to fit inside the cage in a second retracted position and deploy from the cage in a generally inferior direction to a second extended position in which the second portion of the second keel is disposed inferior to the cage of the implant;
wherein the first keel is oriented with the first flange and the second flange extending in a first direction;
wherein the second keel is oriented with the third flange and the fourth flange extending in a second direction substantially opposite the first direction;
wherein the first flange and the second flange extend in the first direction away from the second keel; and
wherein the third flange and the fourth flange extend in the second direction away from the first keel.

2. The implant of claim 1, wherein the first keel is configured to deploy at an angle less than 90° relative to a superior surface of the cage.

3. The implant of claim 2, wherein the first keel is configured to deploy at an angle of approximately 45° with respect to the superior surface of the cage.

4. The implant of claim 1, wherein the second keel is configured to deploy at an angle less than 90° relative to an inferior surface of the cage.

5. The implant of claim 4, wherein the second keel is configured to deploy at an angle of approximately 45° with respect to the inferior surface of the cage.

6. The implant of claim 1, wherein the first edge of the first blade is configured to deploy at a first angle less than 90° relative to a superior surface of the cage;
wherein the first edge of the second blade is configured to deploy at a second angle less than 90° relative to an inferior surface of the cage; and
wherein the first angle is substantially the same as the second angle, such that the first edge of the first blade is substantially parallel to the first edge of the second blade.

7. The implant of claim 1, wherein, in the first retracted position, a tip of the first blade protrudes beyond a superior surface of the cage.

8. The implant of claim 1, wherein, in the second retracted position, a tip of the second blade protrudes beyond an inferior surface of the cage.

9. An intervertebral cage implant, comprising:
a cage configured to be implanted between two vertebrae;
a first deployable keel, including a first blade, a first flange extending at an angle from a first edge of the first blade, and a second flange extending at an angle from a second edge of the first blade; and
a second deployable keel, including a second blade, a third flange extending at an angle from a first edge of the second blade, and a fourth flange extending at an angle from a second edge of the second blade;
wherein a first portion of the first keel is configured to fit inside the cage in a first retracted position and deploy from the cage in a generally superior direction to a first extended position in which the first portion of the first keel is disposed superior to the cage of the implant;
wherein a second portion of the second keel is configured to fit inside the cage in a second retracted position and deploy from the cage in a generally inferior direction to a second extended position in which the second portion of the second keel is disposed inferior to the cage of the implant;
wherein the first keel is oriented with the first flange and the second flange extending in a first direction;
wherein the second keel is oriented with the third flange and the fourth flange extending in a second direction substantially opposite the first direction;
wherein the first flange and the second flange extend in the first direction away from the second keel; and
wherein the third flange and the fourth flange extend in the second direction away from the first keel.

10. The implant of claim 9, wherein, in the first retracted position, a tip of the first blade protrudes beyond a superior surface of the cage.

11. The implant of claim 9, wherein, in the second retracted position, a tip of the second blade protrudes beyond an inferior surface of the cage.

* * * * *